(12) United States Patent
Goldman et al.

(10) Patent No.: US 7,405,076 B2
(45) Date of Patent: Jul. 29, 2008

(54) GENERATION AND USE OF DENDRITIC CELLS

(75) Inventors: Michel Goldman, Brussels (BE); Emmanuel Bartholomé, Wemmel (BE); Christel Buelens, Brussels (BE); Fabienne Willems, Linkebeek (BE)

(73) Assignee: Universite Libre de Bruxelles, Bruxelles (BE)

( * ) Notice: Subject to any disclaimer, the term of this patent is extended or adjusted under 35 U.S.C. 154(b) by 356 days.

(21) Appl. No.: 10/416,434

(22) PCT Filed: Nov. 14, 2001

(86) PCT No.: PCT/EP01/13189

§ 371 (c)(1), (2), (4) Date: May 9, 2003

(87) PCT Pub. No.: WO02/40646

PCT Pub. Date: May 23, 2002

(65) Prior Publication Data

US 2004/0037807 A1 Feb. 26, 2004

(30) Foreign Application Priority Data

Nov. 14, 2000 (EP) .................. 00870273

(51) Int. Cl.
C12N 5/00 (2006.01)
C12N 5/08 (2006.01)
C12N 5/02 (2006.01)

(52) U.S. Cl. ...................................... 435/372; 435/377

(58) Field of Classification Search ........................ None
See application file for complete search history.

(56) References Cited

U.S. PATENT DOCUMENTS 5,104,653 A * 4/1992 Michalevicz ............... 424/85.6

FOREIGN PATENT DOCUMENTS

WO WO 97 29182 A 8/1997
WO WO 9853048 A1 * 11/1998

OTHER PUBLICATIONS

Caux et al., 1996, Blood, vol. 87: 2376:2385.*
Santini et al., 2000, J. Exp. Med. vol. 191: 1777-1788.*
Wang et al., 1998, J. Immunol. vol. 161: 5516-5524.*
Peprotech Product Information for Recombinant Human IL-3, 2005, p. 1-2.*
Verkijk et al., 1999, J. Immunol. vol. 163: 57-61.*
Janeway and Travers, 1997, Immunobiology, pp. 4:6-4:7, 7:12).*
Santini, S.M., et al., "Type I Interferon as a Powerful Adjuvant for Monocyte-derived Dendritic Cell Development and Activity in Vitro and Hu-PBL-SCID Mice"; J. Exp. Med., The Rockefeller University Press: May 15, 2000, pp. 1777-1788, vol. 191, No. 10.
Bendriss-Vermare, N., et al., "Human thymus contains IFN-alpha-producing CD11c-, myeloid CD11c+, and mature interdigitating dendritic cells"; The Journal of Clinical Investigation, Apr. 2001, pp. 835-844, vol. 107, No. 7.
Rissoan, M.C., et al., "Reciprocal Control of T Helper Cell and Dendritic Cell Differentiation"; Science, Feb. 19, 1999, pp. 1183-1186, vol. 283.
Luft, T., et al, "Type I IFNs Enhance the Terminal Differentiation of Dendritic Cells"; The Journal of Immunology, 1998, pp. 1947-1953, vol. 161.
O'Doherty, U., et al., "Human blood contains two subsets of dendritic cells, one imunologically mature and the other immature"; Immunology, 1994, pp. 487-493, vol. 82.

* cited by examiner

Primary Examiner—G. R. Ewoldt
Assistant Examiner—Amy E Juedes
(74) Attorney, Agent, or Firm—Amster, Rothstein & Ebenstein LLP

(57) ABSTRACT

The present invention relates to an in vitro method for differentiation and maturation of isolated monocytes into IL3-R+ CD11c+ myeloid dendritic cells consisting of incubating the monocytes with a combination of a type I interferon and IL-3.

10 Claims, 15 Drawing Sheets

Figure 1:
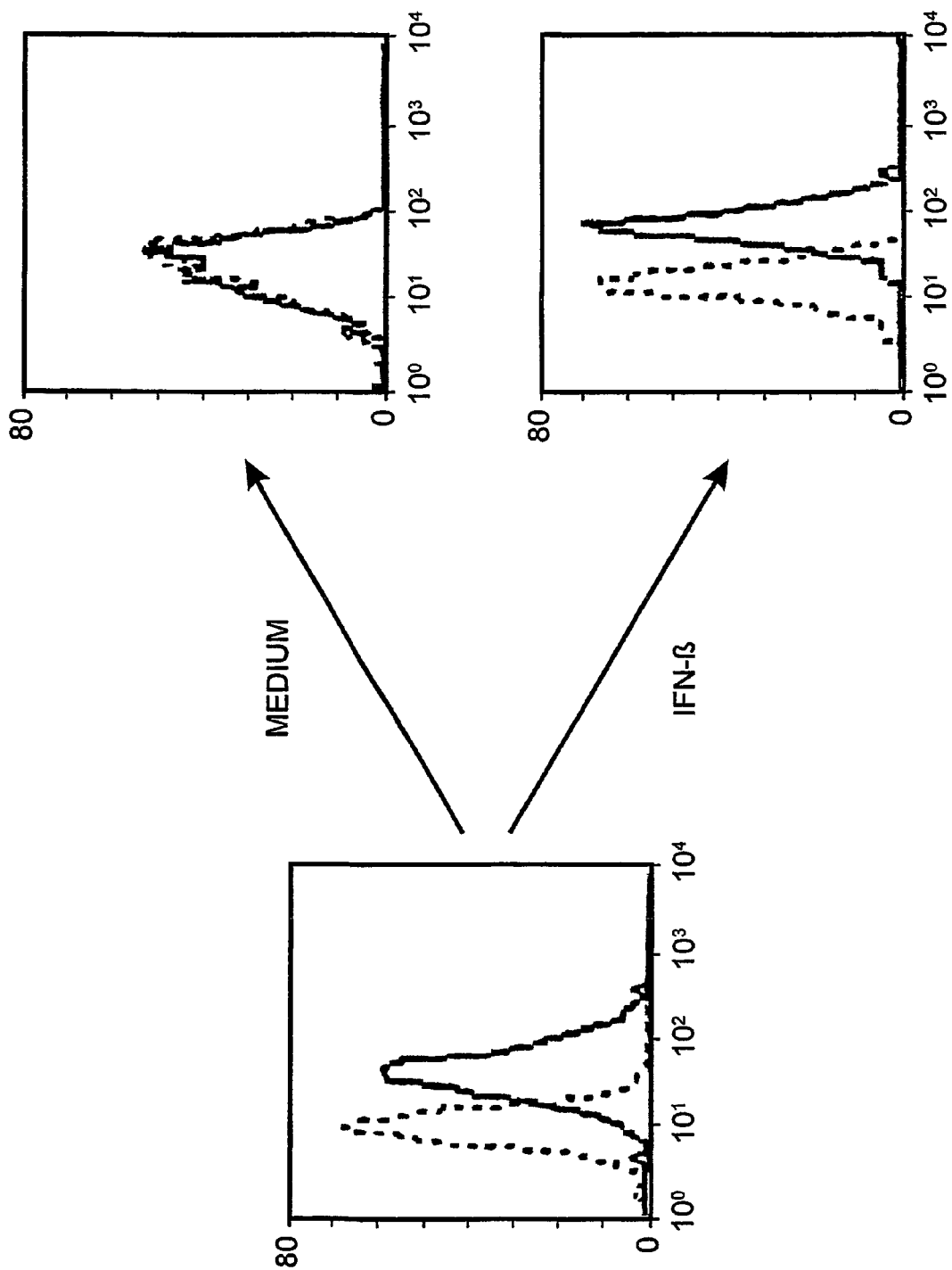

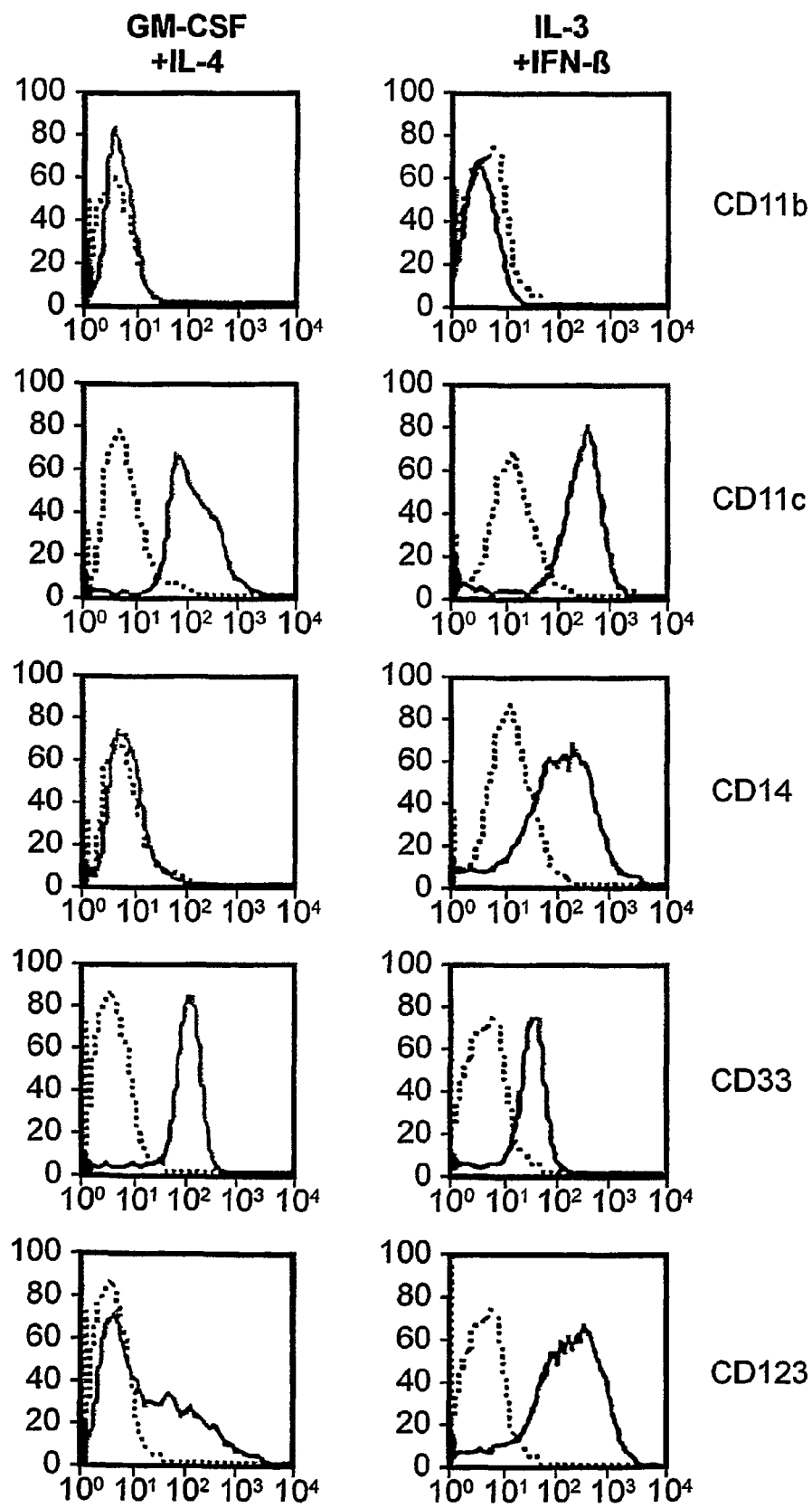
Figure 4A / 1

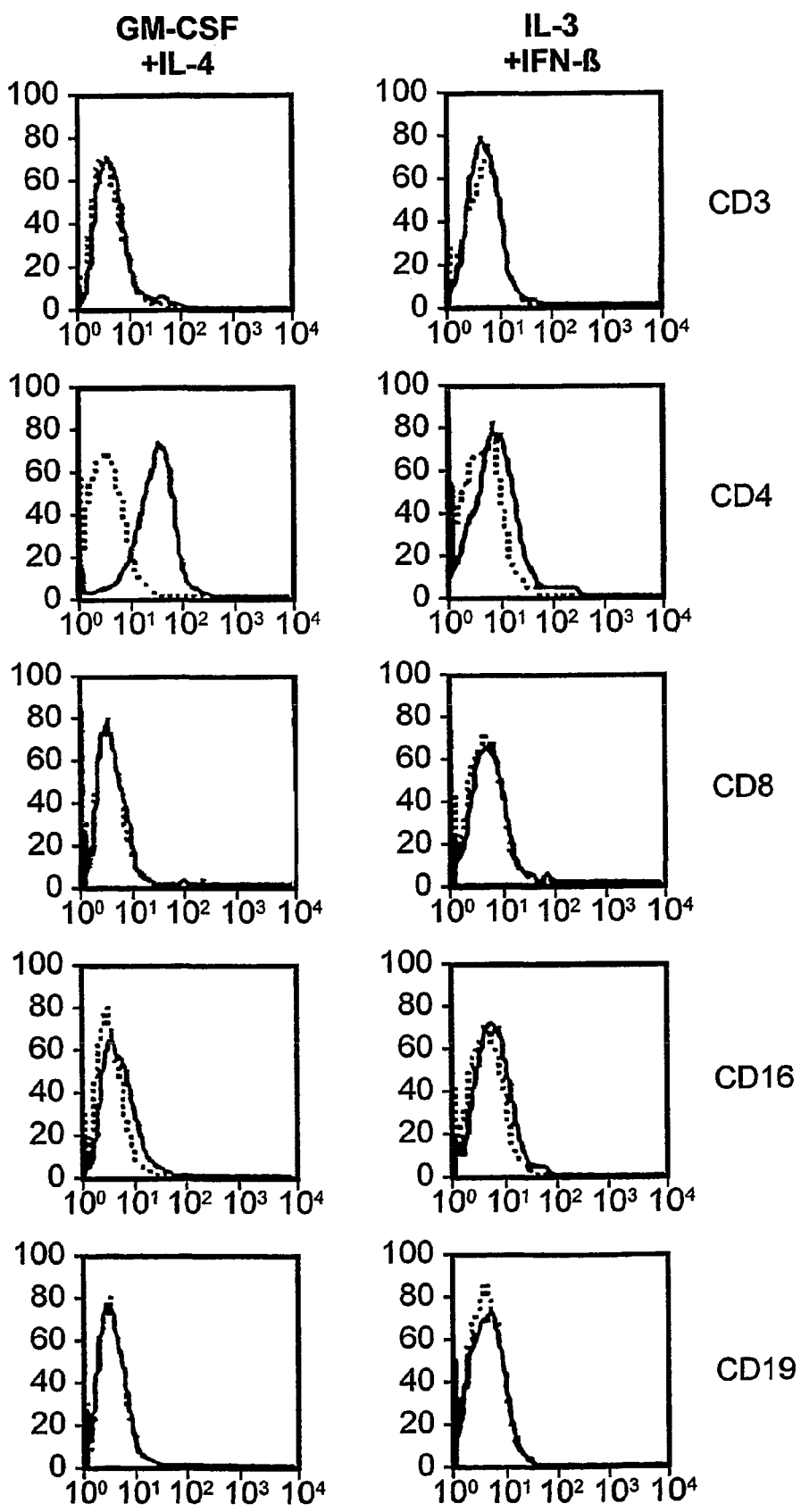
Figure 4A / 2

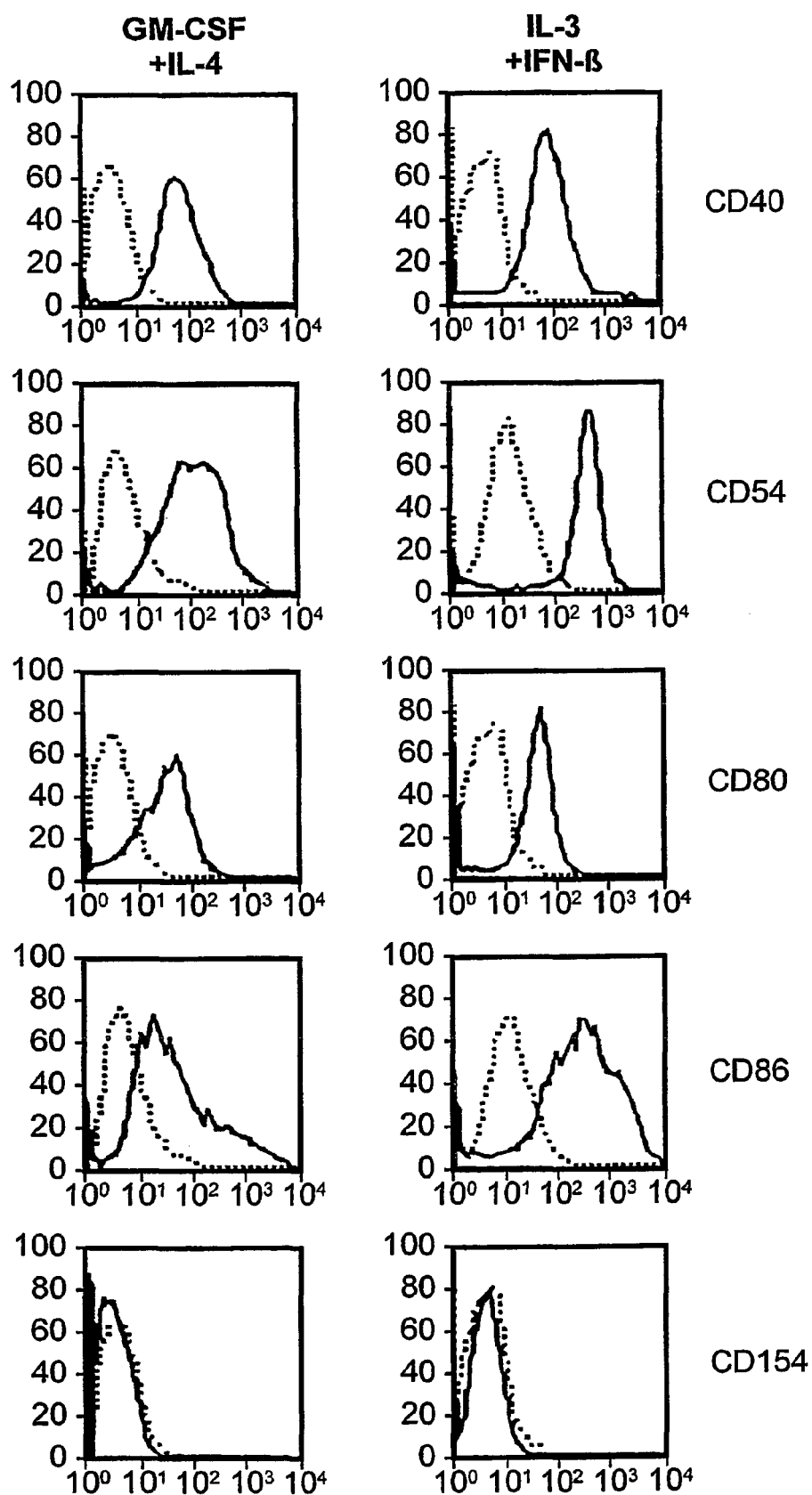
Figure 4A / 3

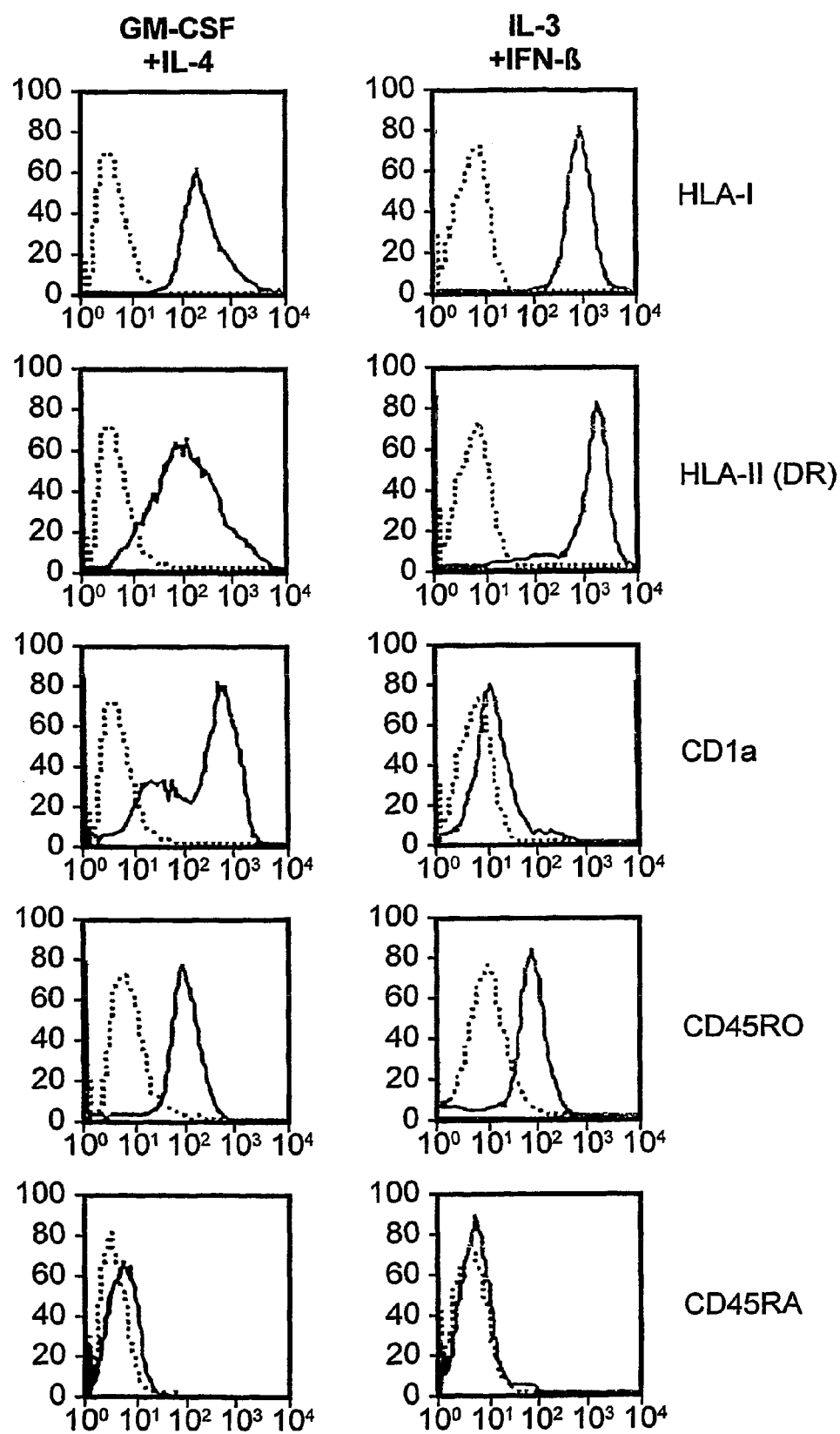
Figure 4A / 4

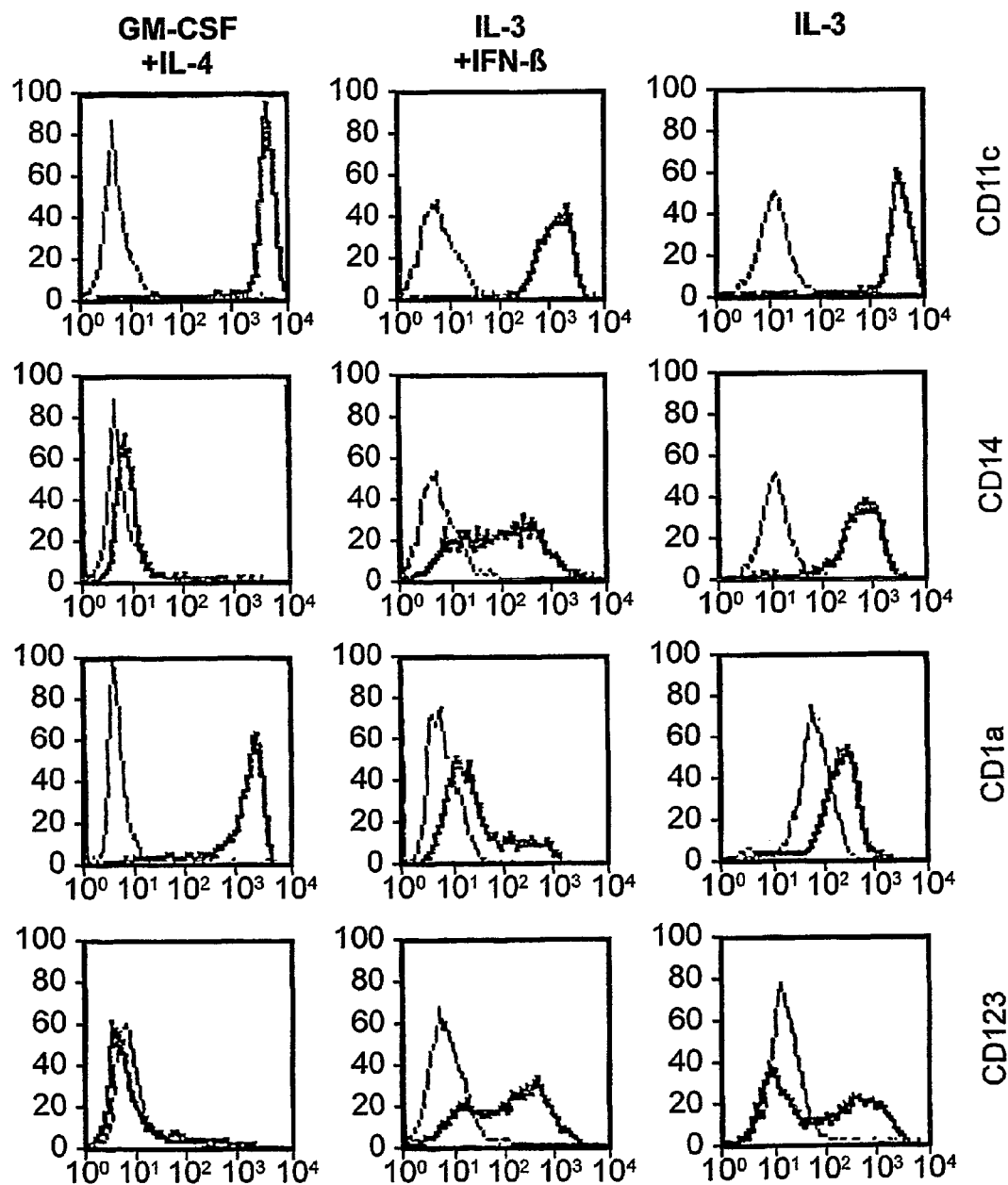
Figure 4B / 1

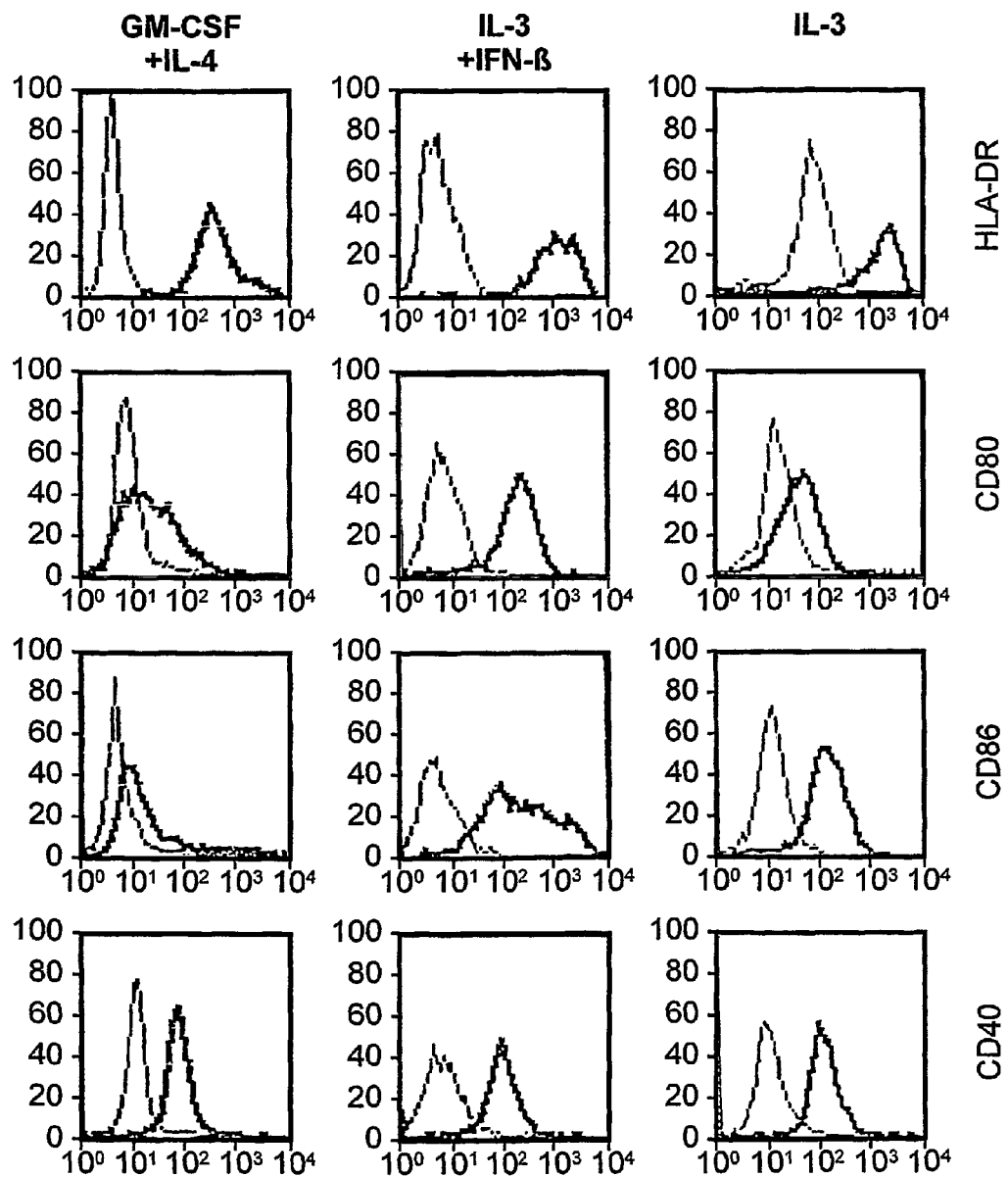
Figure 4B / 2

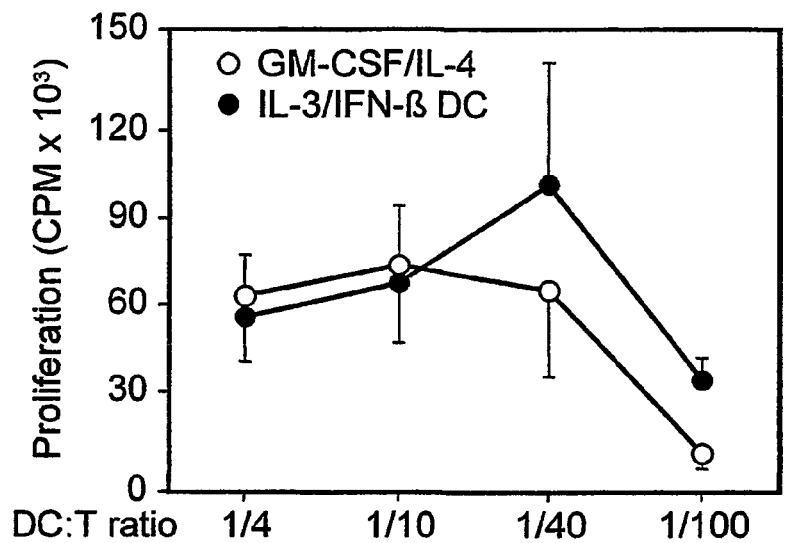
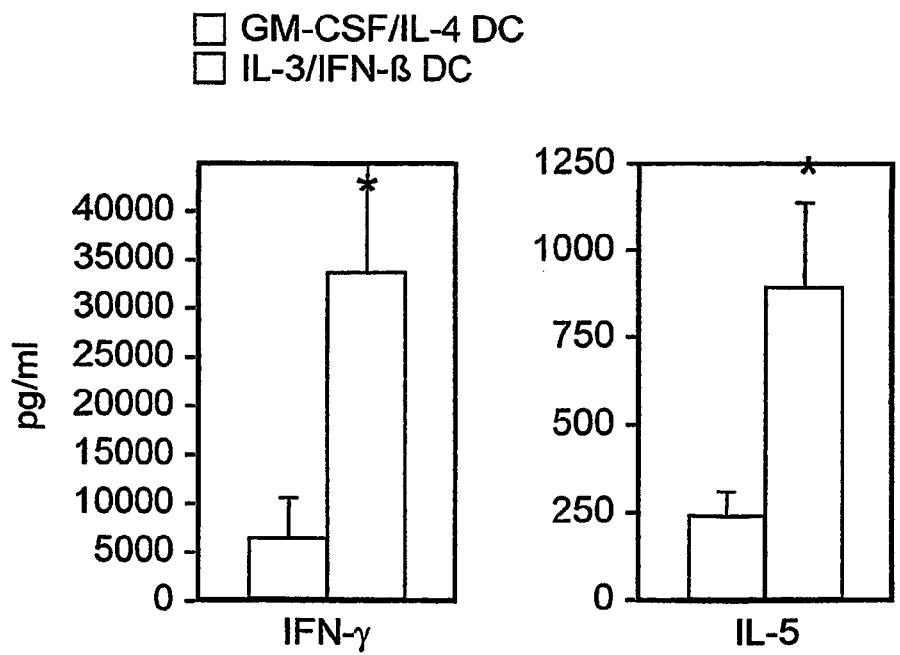
Figure 8

GENERATION AND USE OF DENDRITIC CELLS

This application is a 35 U.S.C. 371 National Stage application of PCT/EP01/13189, published in English under PCT Article 21(2), and claiming the benefit of European Application 00870273.0, filed Nov. 14, 2000. The above applications are incorporated by reference in their entirety.

TECHNICAL FIELD

The present invention relates to the improvement of cell therapy for the treatment or prevention of cancer, infections and autoimmune diseases in particular in the development of new dendritic cells carrying superior character in eliminating or preventing the occurrence of invasive cells.

BACKGROUND ART

Dendritic cells (DC) are key players in the initiation of immune responses. This cell type constitutes the most potent antigen-presenting cell, endowed with the unique capacity to cluster naïve T cells. Consequently, it has been proposed as a natural adjuvant, aiming at the triggering of T-cell responses against poor immunogens, such as tumor-associated Ag (TAA). The realization of clinical trials has long been impaired by the low frequency of circulating DC available in the blood. The development of methods of generating large numbers of DC from hemapoietic precursors has recently allowed the initiation of pioneer clinical trials. These trials have yielded promising results for cancer therapy.

Dendritic cells (DC) represent a major class of antigen-presenting cells characterized by their unique ability to prime naive T cells[1]. Recent works demonstrated the existence of several DC subsets which differentiate from either lymphoid or myeloid bone marrow progenitors[2;3]. A critical factor for myeloid DC development is granulocyte-macrophage colony-stimulating-factor (GM-CSF)[4;5] whereas lymphoid DC are dependent on interleukin (IL)-3 for their survival[6;7]. On the basis of the expression of myeloid markers (i.e. CD11c) or IL-3 receptor-α (IL-3Rα) chain (CD123) expression, two types of DC precursors have been isolated from human peripheral blood[7]. One subtype displays myeloid surface markers and low levels of IL-3Rα, whereas another subtype of putative lymphoid origin express IL-3Rα, is exquisitely dependent on IL-3 for its survival and is a strong producer of type I interferons (IFNs).

Human myeloid DC can be easily generated in vitro by culturing monocytes in presence of GM-CSF and IL-4[4;5] whereas the so-called lymphoid DC have been obtained by isolation of precursors from blood or lymph nodes[6;7].

The GM-CSF/IL4 DC have been used in clinical trials in cell therapy[44]. However, using these conditions, only 67% of immunized patients showed an increase in response to the treatment. Therefore it is important to improve the method, conditions or substances to improve the efficacity of the treatment.

SUMMARY OF THE INVENTION

The present invention is directed towards providing a method for the production of superiour dendritic cells which can be used in cell therapy to eliminate or prevent more efficiently the deleterious effects of invasive cells in patients. The inventors found surprisingly that when monocytes were incubated in specific conditions in presence of IL3 and IFN-β a superior type of DC could be produced.

Type I IFNs are produced by several cell types in response to viral, bacterial and protozoan infections[8-13]. Through their multiple effects on natural killer cells and T cells, type I IFNs represent a critical link between innate and acquired immunity[14]. Recent studies indicate that type I IFNs might also influence DC differentiation and maturation[15;16]. Indeed, IFN-β was shown to promote monocyte differentiation into short-lived DC rapidly undergoing apoptosis[16]. Present inventors investigated whether apoptosis could be stopped using IL-3. To study this, the inventors determined the effect of IFN-β on the expression of IL-3Rα on monocytes and characterized the phenotype and T cell stimulatory capacity of cells derived from monocytes cultured in presence of IL-3 and IFN-β. The present inventors found surprisingly that indeed IL-3 could rescue IFN-β treated cells. In addition these cells seemed to be superior in inducing the immune system.

A particular object of the present invention is directed towards a new type of stable dendritic cell (DC) which is more mature and is more potent in activating the immune system compared to other known stable DCs. Monocytes cultured in IL3 and IFN-β differentiate into dendritic cells with potent T cell stimulatory activities. This invention derives from the original and unexpected finding that IFN-β maintains IL3R expression on monocytes. IL3 allows survival of DC which are short-lived when generated in IFN-β alone and are therefore not suitable for cell therapy. These cells induce both TH1-type (IFN-γ) and TH2-type responses (IL-5), which might be especially advantageous in cancer immunotherapy. These cells directly induce apoptosis of certain tumor cells. The present inventors propose to use those cells for cancer immunotherapy and vaccination against infectious pathogens either by loading the DCs ex vivo with tumor proteins, peptides, gene-transfer (RNA, DNA), fusion with tumor cells (hybrids), followed by the in vivo injection, or to inject the cell directly in the tumor where they could induce the release of tumor antigens through their killing activity.

These aims have been met by following embodiments.

DETAILED DESCRIPTION OF THE INVENTION

Figure 5:
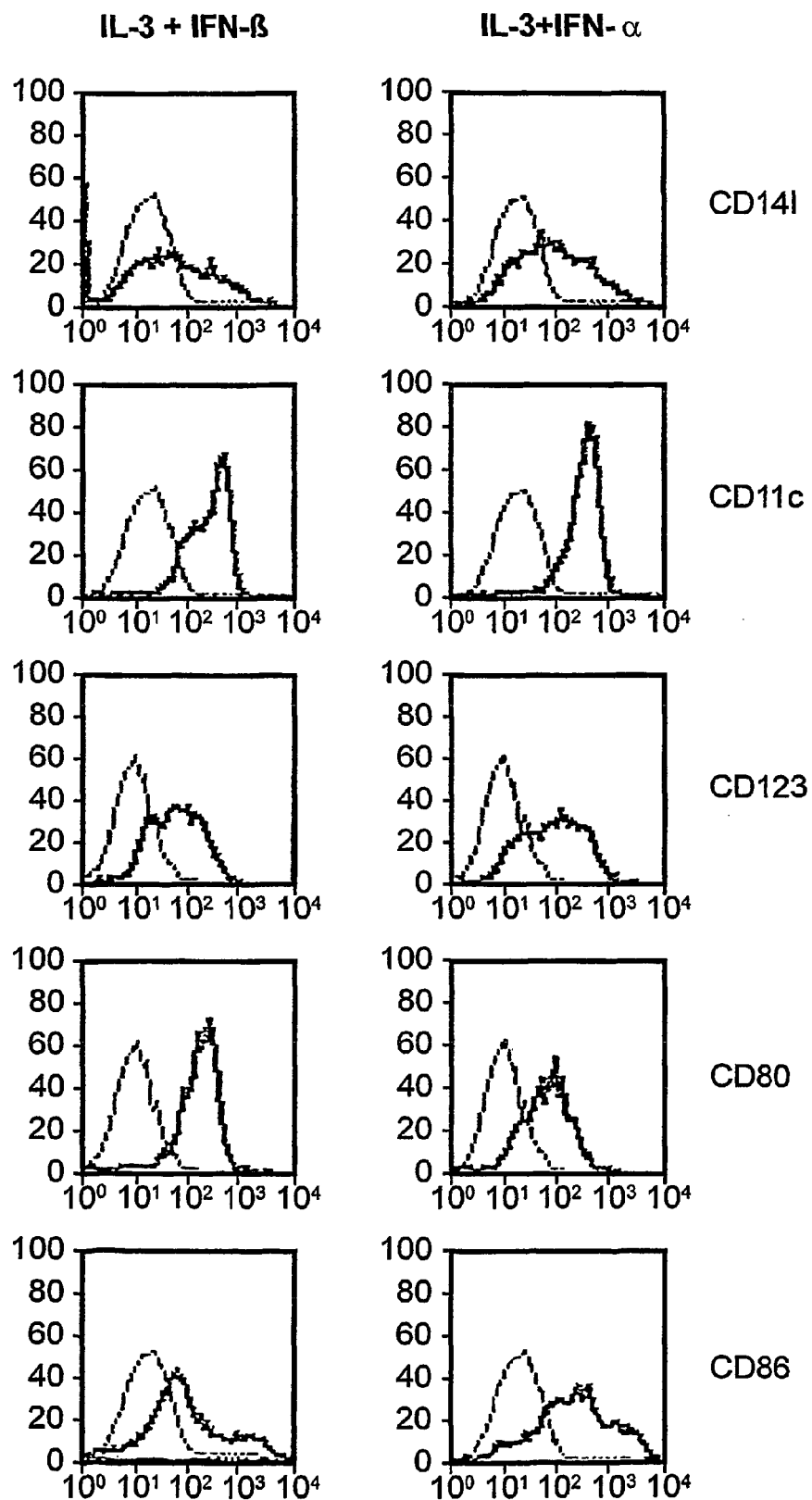

The present invention relates to a method for differentiation and maturation of monocytes into IL3-R+ CD11c+ myeloid dendritic cells comprising incubating said monocytes with a combination of IFN-β and IL-3 (or IL3), or functional analogues thereof. With functional analogues it is meant IFN-α or other type I IFNs as known by a skilled person in the art; also peptidomimetic molecules might be used for this purpose. The inventors proved that IFN-α exerts a similar effect as IFN-β, as the IL-3+IFN-α combination also resulted in the generation of a comparable myeloid IL-3Rα-positive DC (FIG. 5). When monocytes were cultured in IL-3 alone, the inventors found that they expressed lower levels of CD80 and CD86 and higher levels of CD14 than (L-3/IFN-β DC (FIG. 4), which suggests that they are more close to macrophages.

The IL-3/IFN-β DC (or IFN-β/IL-3 DC) cell type resulting from said method is new and differs significantly from previous obtained stable IL4/GM-CSF DC. Monocytes purified from PBMC (peripheral blood mononuclear cells), which are the precursor cells of DC, express IL-3Rα (CD123) but lose this expression after culture in medium alone. Present results shows that the loss of IL-3Rα expression was prevented when IFN-β was added during the culture. Nevertheless, more than 90% of monocytes cultured in medium alone or in presence of IFN-β were found to undergo apoptosis. The inventors found surprisingly that the addition of IL-3 in the presence of IFN-β dramatically enhanced cell survival. Indeed, more than 65% of cells were still alive using these culturing conditions. Present inventors found surprisingly that IL-3 rescue monocytes cultured in the presence of IFN-β from apoptosis, and allows them to further differentiate. These observations demonstrate a cooperating effect of IL-3 and IFN-β on cell survival and differentiation. The effect of type I IFNs on IL-3Rα expression has never been assessed before.

To characterize the cells obtained by culture of monocytes in IL-3 and IFN-β, the present inventors first looked at their ultrastructural morphology and found that monocytes cultured under the conditions acquired cytoplasmic expansions of the dendritic type. Cells derived from monocytes cultured in IL-3 and IFN-β can therefore be referred to hereafter as IL-3/IFN-β DC or IFN-β/IL-3 DC.

The present inventors further characterized that IL-3/IFN-β DC expressed markers of the myeloid lineage (CD11c, CD14, and CD33). They also expressed high levels of HLA class I and class II molecules, CD40, CD54, CD 80 and CD86, and IL-3Rα (CD123). Contrary to IL-4/GM-CSF DC, IL-3/IFN-β DC showed much higher levels of IL-3Rα. Conversely, CD1a was expressed on IL4/GM-CSF DC but not on cells derived from monocytes cultured in IL-3 and IFN-β. The present results therefore indicated that IL-3/IFN-βDC are also myeloid but phenotypically completely different cells compared to the known IL4/GM-CSF DC. Based on their markers IL-3/IFN-β DCs may also be referred as IL3-R+ CD11c+ dendritic cells (DC) or IL3-R+ CD11c+ myeloid dendritic cells.

Advantageously, IL-3 and IFN-β can be added to the monocytes simultaneously, sequentially or separately.

According to the invention IFN-β is present at a concentration of between 10 and 20000 U/ml.

The present results demonstrates that the loss of IL-3Rα expression was prevented by adding 1000 U/ml IFN-β in the culture medium. Nevertheless, concentrations of 10, 15, 20, 25, 30, 35, 40, 45, 50, 55, 60, 65, 70, 75, 80, 85, 90, 95,100, 150, 200, 250, 300, 350, 400, 450, 500, 550, 600, 650, 700, 750, 800, 850, 900, 950, 1000, 1100, 1150, 1200, 1250, 1300, 1350, 1400, 1450, 1500, 1550, 1600, 1650, 1700, 1750, 1800, 1850, 1900, 1950, 2000, 2100, 2150, 2200, 2250, 2300, 2350, 2400, 2450, 2500, 2550, 2600, 2650, 2700, 2750, 2800, 2850, 2900, 2950, 3000, 3100, 3150, 3200, 3250, 3300, 3350, 3400, 3450, 3500, 3550, 3600, 3650, 3700, 3750, 3800, 3850, 3900, 3950, 4000, 4100, 4150, 4200, 4250, 4300, 4350, 4400, 4450, 4500, 4550, 4600, 4650, 4700, 4750, 4800, 4850, 4900, 4950, 5000, 5100, 5150, 5200, 5250, 5300, 5350, 5400, 5450, 5500, 5550, 5600, 5650, 5700, 5750, 5800, 5850, 5900, 5950, 6000, 6100, 6150, 6200, 6250, 6300, 6350, 6400, 6450, 6500, 6550, 6600, 6650, 6700, 6750, 6800, 6850, 6900, 6950, 7000, 7100, 7150, 7200, 7250, 7300, 7350, 7400, 7450, 7500, 7550, 7600, 7650, 7700, 7750, 7800, 7850, 7900, 7950, 8000, 8100, 8150, 8200, 8250, 8300, 8350, 8400, 8450, 8500, 8550, 8600, 8650, 8700, 8750, 8800, 8850, 8900, 8950, 9000, 9100, 9150, 9200, 9250, 9300, 9350, 9400, 9450, 9500, 9550, 9600, 9650, 9700, 9750, 9800, 9850, 9900, 9950, 10000, 10050, 10100, 10150, 10200, 10250, 10300, 10350, 10400, 10450, 10500, 10550, 10600, 10650, 10700, 10750, 10800, 10850, 10900, 10950, 11000, 11050, 11100, 11150, 11200, 11250, 11300, 11350, 11400, 11450, 11500, 11550, 11600, 11650, 11700, 11750, 11800, 11850, 11900, 11950, 12000, 12050, 12100, 12150, 12200, 12250,.12300, 12350, 12400, 12450, 12500, 12550, 12600, 12650, 12700, 12750, 12800, 12850, 12900, 12950, 13000, 13050, 13100, 13150, 13200, 13250, 13300, 13350, 13400, 13450, 13500, 13550, 13600, 13650, 13700, 13750, 13800, 13850, 13900, 13950, 14000, 14100, 14150, 14200, 14250, 14300, 14350, 14400, 14450, 14500, 14550, 14600, 14650, 14700, 14750, 14800, 14850, 14900, 14950, 15000, 15050, 15100, 15150, 16200, 15250, 15300, 15350, 15400, 15450, 15500, 15550, 15600, 15650, 15700, 15750, 15800, 15850, 15900, 15950, 16000, 16050, 16100, 16150, 16200, 16250, 16300, 16350, 16400, 16450, 16500, 16550, 16600, 16650, 16700, 16750, 16800, 16850, 16900, 16950, 17000, 17100, 17150, 17200, 17250, 17300, 17350, 17400, 17450, 17500, 17550, 17600, 17650, 17700, 17750, 17800, 17850, 17900, 17950, 18000, 18050, 18100, 18150, 18200, 18250, 18300, 18350, 18400, 18450, 18500, 18550, 18600, 18650, 18700, 18750, 18800, 18850, 18900, 18950, 19000, 19050, 19100, 19150, 19200, 19250, 19300, 19350, 19400, 19450, 19500, 19550, 19600, 19650, 19700, 19750, 19800, 19850, 19900, 19950 and 20000 U/ml are possible.

According to a preferred embodiment of the invention IFN-β is given at a concentration of 1000 U/ml.

According to the invention IL-3 is present at a concentration between 1 and 1000 U/ml. In this respect, concentrations of 1, 2, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 705, 710, 715, 720, 725, 730, 735, 740, 745, 750, 755, 760, 765, 770, 775, 780, 785, 790, 795, 800, 805, 810, 815, 820, 825, 830, 835, 840, 845, 850, 855, 860, 865, 870, 875, 880, 885, 890, 895, 900, 905, 910, 915, 920, 925, 930, 935, 940, 945, 950, 955, 960, 965, 970, 975, 980, 985, 990, 995 and 1000 U/ml are possible.

According to a preferred embodiment of the invention, IL-3 is present at a concentration of 50 U/ml.

According to the present invention the method to provide a population of IL3-R+ CD11c+ myeloid dendritic cells comprises at least the following steps:
(a) isolating monocytes from a patient, and,
(b) incubating said monocytes in the presence of IFN-β and IL-3 or functional analogues thereof.

There are two main sources of DC precursors: CD34+ stem cells and peripheral blood (PB) monocytes. The main constraints of generating DC from stem cells is that the culture time is long and obtaining CD34+ cells requires mobilization of the patient. Therefore a preferred embodiment of the present invention is to use monocytes as a DC precursor. These cells can normally, when present in blood, differentiate into DC in presence of GM-CSF or as the present inventors showed in presence of IL3-IFN-β. Different techniques might be used to isolate monocytes from the blood as known by the person skilled in the art. A preferred method is described in example 1. With the term "population" is meant IL3-R+ CD11c+ myeloid dendritic cells as such, a group of IL3-R+ CD11c+ myeloid dendritic cells which may be different in other characteristics, or a group of cells comprising IL3-R+ CD11c+ myeloid dendritic cells. Also one cell is not excluded from this definition. It is important to mention that, the inventors do not exclude the fact that monocytes can be further differentiated and maturated in vivo by injecting IL-3 and IFN-β as such into the patient.

According to present invention IL3-R+ CD11c+ myeloid dendritic cells may further be treated to produce antigen presenting dendritic cells. Consequently the method as described by the present invention comprises at least the following steps:
(a) isolating monocytes from a patient,
(b) incubating said monocytes in the presence of IFN-β and IL-3 producing IL3-R+ CD11c+ myeloid dendritic cells, and,
(c) presenting an antigen on the surface of said dendritic cells.

Depending on the specific treatment as described below, antigens are specific molecules present on cells selected from the group consisting of a cancer cell, a bacteria, a parasitically infected cell and a virally infected cell. These antigens can be large molecules which are processed by the DC to load MHC molecules, or can be smaller molecules (i.e. peptides) which are immediately loaded onto the MHC molecules. Several approaches have been used to arm DC with target antigen for use in clinical trials. Methods used to approach this step of antigen loading are reviewed by Fong and Engleman[44]. Inventors also point out that, IL3-R+ CD11c+ myeloid dendritic cells can be produced in vivo by injecting IL-3 and IFN-β or IL-3 and IFN-β in combination with an antigen into the patient. The capacity of presenting a peptide on the surface of said dendritic cells according to present invention can for example be achieved by contacting said dendritic cell with at least part of an antigen differentially expressed on a cell. This cell can be a cell selected from the group consisting of a cancer cell, a bacterial cell, a parasitically infected cell and a virally infected cell. Antigens are delivered from these to the DC resulting in the activation of the DCs.

Alternatively, the capacity of presenting a peptide on the surface of said dendritic cells can be achieved by pulsing said dendritic cells with antigenic proteins, by loading said dendritic cells with antigenic peptides or can be achieved by transforming/transducing said dendritic cells by nucleic acid molecules coding for at least part of said antigen. With "pulsing" is meant that DC are activated by these antigens and enter into the MHC class II and/or MHC class I processing pathway. Transformation of DC can be achieved using electric pulses, liposomes or other techniques as known by the person skilled in the art. Viral vectors allow the transduction of cells. With viral vectors also retroviral, adenoviral and adeno-associated vectors are meant.

Transformation/transduction of the cells allows introduction of DNA encoding the antigen and when appropriate expression signals are present said antigen is made in the cell and brought through the endogenous mechanisms to the surface of the transformed/transduced dendritic cell. As a result of this an antigen-presenting IL3-R+ CD11c+ myeloid dendritic cells is made.

Alternatively, the capacity of presenting a peptide on the surface of said dendritic cells is achieved by fusing said dendritic cell with cells carrying specific antigens. The production of dendritic-like cell/tumor cell hybrids and hybridomas for inducing anti-tumor response have been described in WO96/30030. This document provides dendritic-like cell/tumor cell hybridomas and pluralities of dendritic-like cell/tumor cell hybrids that confer tumor resistance in vivo. The hybrids and hybridomas are generated by the fusion of tumor cells with dendritic-like cells. For instance, immortal tumor cells from an autologous tumor cell line can be fused with autologous or HLA-matched allogeneic dendritic-like cells. Autologous tumor cell lines can be derived from primary tumors and from their metastases. Alternatively, immortal dendritc-like cells from an autologous or allogeneic HLA-matched dendritic-like cell line can be fused with autologous tumor cells. Autologous dendritic-like cell lines can be prepared from various sources such as peripheral blood and bone marrow. Dendritic-like cell/tumor cell hybridomas and pluralities of hybrids can be directly infused for active immunization of cancer patients against their residual tumor cells. The hybridomas and hybrids can also be used for the in vitro activation of autologous immune cells before their reinfusion into the patient for passive immunization against the tumor cells.

The present invention also proposes a method to provide an activated population of T cells using antigen-presenting IL3-R+ CD11c+ myeloid dendritic cells obtainable by a method as described above comprising at least the following steps:

(a) isolating monocytes from a patient,
(b) incubating said monocytes in the presence of IFN-β and IL-3 to provide a population of IL3-R+ CD11c+ myeloid dendritic cells,
(c) presenting an antigen (for instance peptide or protein) on the surface of said dendritic cells, thereby providing a population of antigen presenting dendritic cells; and,
(d) activating a population of T cells with said population of antigen presenting dendritic cells.

An activated T cell being a T cell (CD3+ cell) proliferating and/or secreting cytokines (IL-2, IL4, IL-5, IFN-γ, etc.) and/or expressing activation markers (CD25, CD69, HLA-DR, CD40L, etc.). Indeed, the present inventors indicated that the low levels of IL-12 secreted by IL-3/IFN-β DC contribute to their ability to elicit IFN-γ production by T cells. In addition, the inventors proved that, IL-3/IFN-β DC also induced IL-5 production in mixed leucocyte culture and were also much more efficient than IL-4/GM-CSF DC in that respect. If necessary, an activated T cell can always be separated from the antigen presenting dendritic cell by cell sorting.

In preferred methods according to present invention said T cell is a T helper cell.

The invention also refers to a method wherein the steps of producing a population of cells as described above such as IL3-R+ CD11c+ myeloid dendritic cells and/or antigen presenting IL3-R+ CD11c+ myeloid dendritic cells and/or activated T cells using antigen presenting IL3-R+ CD11c+ myeloid dendritic cells occur in vitro and/or in vivo.

The present invention also provides a population of IL3-R+ CD11c+ myeloid dendritic cells, a population of antigen-presenting IL3-R+ CD11c+ myeloid dendritic cells or a population of activated T cells obtainable by a method as described above, or a combination thereof.

The present inventors showed that, although IL-3/IFN-β DC display several features suggestive of a higher degree of maturation, they should not be considered as fully mature. Indeed, the inventors gave evidence that the IL3-R+ CD11c+ myeloid dendritic cells according to present invention can be further stimulated using a stimulant. The present invention also refers to a method to further stimulate a population of IL3-R+ CD11c+ myeloid dendritic cells, whereby said dendritic cells are additionally incubated with a stimulant. This incubation can be performed simultaneously, sequentially or separately from the cytokine treatment. With stimulation is also meant maturation, induction and/or activation. According to present invention, said stimulant may be chosen from a group comprising virus, bacterium, LPS (lipopolysaccharide), nucleic acid, functional derivatives or a combination thereof. The term "nucleic acids" refers to a single stranded or double stranded nucleic acid sequence, said nucleic acid may consist of deoxyribonucleotides (DNA) or ribonucleotides (RNA) or may be amplified cDNA or amplified genomic DNA. Consequently, the present invention also relates to a population of stimulated IL3-R+ CD11c+ myeloid dendritic cells obtainable by a method according to present invention. In the examples, the inventors showed that when analyzing the IFN-α production by IL-3/IFN-β DC, stimuli such as LPS and formaldehyde-inactivated influenza virus induced said DC only to a lower extent (table 2). Contrarily, Poly (I:C), which mimicks viral double-stranded RNA, was able to induce IFN-α production by IL-3/IFN-β DC to a higher extent. It has to be understood that all applications (such as methods, compositions, kits, uses) suggested in present invention for unstimulated IL-3/IFN-β DC may be applied for stimulated IL-3/IFN-β DC.

The present invention relates to a composition for use as a medicament or cell based product intended for clinical use comprising at least one of the following combinations of components:

IL-3 and IFN-β or functional analogues thereof,

IL-3 and IFN-β or functional analogues thereof mixed with antigen and/or stimulant, a population of monocytes mixed with IL-3 and IFN-β or functional analogues thereof, a population of monocytes mixed with IL-3, IFN-β or functional analogues thereof and antigen and/or stimulant, a population of IL3-R+ CD11c+ myeloid dendritic cells, a population of IL3-R+ CD11c+ myeloid dendritic cells mixed with antigen and/or stimulant, a population of antigen-presenting IL3-R+ CD11c+ myeloid dendritc cells, or, a population of activated T cells obtainable using antigen-presenting IL3-R+ CD11c+ myeloid dendritic cells, whereby said IL3-R+ CD11c+ myeloid dendritic cells are unstimulated or stimulated using a method according to present invention, or a combination thereof.

Cell based products are not yet considered as medicament and could be considered as transfusion products in the future.

The present results also showed that the IL-3/IFN-β DC have endocytosis capacity. IL-3/IFN-β DC spontaneously secreted IL-6, IL-8, IL-12 (p40) and TNFα.

The inventors also studied the cytokine production of GM-CSF/IL-4 DC versus IL-3/IFN-β DC. As compared to GM-CSF/IL-4 DC, IL-3/IFN-β DC produced less IL-12 (p40) whereas their secretion of IL-8 was slightly higher. As it is the case for IL-4/GM-CSF DC, both LPS and CD40 ligation induced by CD40L transfectants upregulated the synthesis of cytokines by IL-3/IFN-β DC. As compared to GM-CSF/IL-4 DC, IL-3/IFN-β DC produced similar levels of TNFα and IL-6 levels under both conditions of stimulation, higher IL-8 levels in response to CD40L but not to LPS, and much lower levels of IL-12 (p40) and IL-12 (p70) whatever the stimulus considered.

At all stimulator/responder ratios, IL-3/IFN-β DC were as efficient as GM-CSF/IL-4 DC to induce naive CD4+ T cell proliferation. Nevertheless, if the inventors considered the profile of cytokines secreted by T cells upon exposure to allogenic DC, IL-3/IFN-β DC induced the production of substantial amounts IFN-γ, despite their low synthesis of IL-12. In addition, IL-3/IFN-β DC also elicited IL-5 production and were significantly more efficient than IL4/GM-CSF DC in that respect.

Despite their low level of IL-12 production, IL-3/IFN-β DC stimulate high level of IFN-γ production from adult CD4+ T cells, suggesting that they use other factors or membrane molecules to elicit the synthesis of Th1 cytokines. Indeed IL-12 independent pathways of IFN-γ were recently described[13;14;28;29]. Taken together, these data indicate that IL-3/IFN-β DC differ from the CD4+ CD3− CD11c− IL-3Rα+ plasmacytoid cells isolated from peripheral blood described by Grouard et al.[6], as the latter cells proved to be poor inducers of IFN-γ in MLR.

The present inventors conclude that upon using above described methods new types of DC can be formed which are more mature than previously described myeloid DC and which have a superior character in inducing T cell expression. Increased cytokine expression results in a more rapid and efficient stimulation of the immune system, and therefore will be more efficient in eliminating foreign infectious material in a patient.

Monocyte-derived DC primed with tumor antigens are now clinically used in several protocols to induce specific antitumor immunity[30-32]. Both Th1 and Th2 effector mechanisms have been shown to collaborate with each other in directing an effective antitumor activity[33]. Because of their ability to induce both Th1 and Th2 type responses, the inventors suggest that IFN-β/IL-3 DC (induced or uninduced) might be appropriate to induce efficient tumor immunity.

Preferably, a composition according to the invention is supplemented with at least one additional cytokine. According to the present invention, said cytokine is preferentially chosen from a group comprising IFN-α, IFN-β, IL-3 and IL-12. IL-12 and IFN-α are pivotal cytokines for Th1 differentiation and generation of cytotoxic T cells endowed with potent anti-tumor effects.

The invention implies the preparation of a medicament for treating cancer, infections and autoimmune diseases comprising a composition as described above. Investigations showed that the immunologic and clinical effects of antigen-loaded dendritic cells administered as a therapeutic vaccine to patients with cancer[44]. Although DC-based vaccination methods are cumbersome, promising results from clinical trials in patients with malignant lymphoma, melanoma, and prostate cancer suggest that immunotherapeutic strategies that take advantage of the antigen-presenting properties of dendritic cells may ultimately prove both efficacious and widely applicable to human tumors. Also the role of DC in initiating or priming immune responses to viral and bacterial antigens in vivo is well established. It has been demonstrated that human DC, but not monocytes or B cells, can sensitise naïve T cells to soluble protein antigens, enabling the generation of antigen-specific CD4+ helper and CD8+ CTL lines in vitro[44]. CD8+ cytotoxic T lymphocytes (CTL) have been demonstrated to recognize and kill cancer cells in various tumor models. The ability of DC to prime T cells capable of recognizing and killing tumor cells in an antigen-specific fashion has been demonstrated in various animal models. Moreover, DC-based immunization can lead to immunologic memory with protection against subsequent tumor challenges. Fong et al (1997[45]) illustrated that immunizing with self proteins could protect animals against autoimmune reactions.

The present invention also relates to the pharmacological composition comprising the composition according to the invention and optionally a pharmaceutical acceptable carrier, diluent or excipient. Pharmaceutically acceptable carriers include any carrier that does not itself induce the production of antibodies harmful to the individual receiving the composition. Suitable carriers are typically large, slowly metabolizing macromolecules such as proteins, polysaccharides, polylactic acids, polyglycolic acids, polymeric amino acids, amino acid copolymers; and inactive virus particles. Such carriers are well known to those of ordinary skill in the art. A "vaccine" is an immunogenic composition capable of eliciting protection against infections, whether partial or complete. A vaccine may also be useful for treatment of an individual, in which case it is called a therapeutic vaccine. Said vaccine compositions may include prophylactic as well as therapeutic vaccine compositions. The term "therapeutic" refers to be capacity of eliminating or preventing invasive cells.

The present invention also relates to a method of killing a target cell comprising contacting said target cell with a composition. This killing can be performed in vitro or in vivo.

Preferably, said target cell is selected from the group consisting of a cancer cell, a bacterial cell, a parasitically infected cell or a virally-infected cell.

The present invention also provides an in vitro screening method using a population of IL3-R+ CD11c+ myeloid dendritic cells, a population of antigen-presenting IL3-R+ CD11c+ myeloid dendritic cells, a population of stimulated IL3-R+ CD11c+ myeloid dendritic cells, a population of stimulated antigen-presenting IL3-R+ CD11c+ myeloid dendritic cells or a population of activated. T cells obtainable by a method as described in present invention. By their potent immunostimulatory properties, DC loaded with tumor or bacterial Ag could be used to activate T cells against unknown poorly immunigenic Ag and thus help to discover them.

According to present invention, a population of myeloid IL3-R+ CD11c+ dendritic cells, a population of antigen-presenting IL3-R+ CD11c+ myeloid dendritic cells, a population of stimulated IL3-R+ CD11c+ myeloid dendritic cells, a population of stimulated antigen-presenting IL3-R+ CD11c+ myeloid dendritic cells or a population of activated T cell using antigen-presenting IL3-R+ CD11c+ myeloid dendritic cells obtainable by a method according to the present invention can be used for the preparation of in vitro screening tests.

According to present invention, a method for detecting T cell mediated activity of a target antigenic peptide comprises at least the following steps:
(a) providing a population of antigen-presenting IL3-R+ CD11c+ myeloid dendritic cells obtainable from monocytes according to a method as described above,
(b) contacting a T cell with said dendritic cell thereby providing an activated T cell,
(c) contacting a target cell with said activated T cell, and,
(d) monitoring the effect of said activated T cell on said target cell, thereby detecting anti-target activity, whereby said IL3-R+ CD11c+ myeloid dendritic cells are unstimulated or stimulated using a method according to the present invention, or a combination thereof.

The present invention also describes a kit for detecting T cell mediated activity of a target antigenic peptide, comprising at least one combination of components chosen from the following list:
IL-3 and IFN-β, or functional analogues thereof,
IL-3 and IFN-β or functional analogues thereof mixed with antigen and/or stimulant,
a population of monocytes mixed with IL-3 and IFN-β or functional analogues thereof,
a population of monocytes mixed with IL-3, IFNβ or functional analogues thereof and antigen and/or stimulant,
a population of IL3-R+ CD11c+ myeloid dendritic cells,
a population of IL3-R+ CD11c+ myeloid dendritic cells mixed with antigen and/or stimulant,
a population of antigen-presenting IL3-R+ CD11c+ myeloid dendritic cells, or
a population of activated T cells obtainable using antigen-presenting IL3-R+ CD11c+ myeloid dendritic cells whereby said IL3-R+ CD11c+ myeloid dendritic cells are unstimulated or stimulated using a method according to the present invention, or a combination thereof.

It has been shown that freezing population of said cells did not alter the functional properties of these cells. Also other methods for storage as known by the skilled person in the art can be applied to preserve these cells[46].

All methods, uses and kits described in the present invention for the detection of T cell mediated activity also relate to the use of a population of IL3-IFN-β DC as reagent for the purpose of following the immune response in patients who got either DC-vaccines or other vaccines. T cells might be isolated from patients and tested using antigen-presenting IL3-IFN-β DC to analyse if the immunologic response in the patient has been activated. For his purpose PBMC (periferal blood mononuclear cells) or purified T cells might be used. This test system allows the evaluation of any therapy against infections, cancer or auto-immune diseases.

The present invention suggests the use of a composition according to the invention as a vaccine adjuvant and the vaccine adjuvant as such comprising a composition according to the invention.

According to present invention a vaccine comprising the composition as described by the invention can be used to immunize humans or animals against different diseases. Vaccination of patients has already been illustrated and found to be efficacious using peptide-pulsed IL4/GM-CSF DC in cancer patients (Toungouz et al. 1999[46]).

In particular, the present invention describes a method for immunizing humans or animals against a disease comprising administering a vaccine comprising an adjuvant as described above.

The present invention also relates to a method of treatment of cancer, infections and autoimmune diseases comprising the use of at least one of the following combinations of components:
IL-3 and IFN-β or functional analogues thereof,
IL-3 and IFN-β or functional analogues thereof mixed with antigen and/or stimulant,
a population of monocytes mixed with IL-3 and IFN-β or functional analogues thereof,
a population of monocytes mixed with IL-3, IFN-β or functional analogues thereof and antigen and/or stimulant,
a population of IL3-R+ CD11c+ myeloid dendritic cells,
a population of IL3-R+ CD11c+ myeloid dendritic cells mixed with antigen and/or stimulant,
a population of antigen-presenting IL3-R+ CD11c+ myeloid dendritic cells, or,
a population of activated T cells obtainable using antigen-presenting IL3-R+ CD11c+ myeloid dendritic cells whereby said IL3-R+ CD11c+ myeloid dendritic cells are unstimulated or stimulated using a method according to the present invention, or a combination thereof.

In the design and conduct of above described applications, important considerations include methods for introducing the antigen into MHC class I and II processing pathways, methods for isolating and activating dendritic cells, route of administration and antigen selection. Because the cell therapy as presented in the present invention needs a specific recognition of the target cell, it is important that indeed the choice of antigen is well considered. Therefore the present invention suggests that the antigen is a tumor specific antigen, an infectious specific antigen or a self-protein when applied in the treatment of cancer, infections (viral, bacterial, parasitical) or autoimmune diseases. In addition, it is important that the compositions are administered to a person in need of treatment in a therapeutically effective amount. Example of antigens that might be considered as tumor antigens are described by Fong and Engleman 2000[44].

According to the present invention said viral disease is selected from the group consisting of for instance HIV, human Papilloma virus, Ebstein Barr virus and Cytomegalovirus.

According to the present invention said autoimmune disease is selected from the group consisting of multiple sclerosis myasthenia gravis, juvenile chronic arthritis, chronic arthritis, LED, atopic dermatitis and juvenile diabetes. Inventors suggest that probably all autoimmune diseases may be treated or prevented by a method as described by the invention.

According to the present invention, said compositions can be injected into patients using different ways. Preferentially injection is carried out intravenously, intra-lymphoidal or intratumoral, nevertheless, other routes can be used such as subcutaneous injections. It is interesting to mention that in addition to expressing the requisite MHC and costimulatory molecules to prime T cells, the DC cells express appropriate adhesion molecules and chemokine receptors to attract the DC to secondary lymphoid organs for priming. In this respect, inefficient priming could be circumvented by injecting DC directly to secundary lympoid organs through intralymphatic or intranodal injection. The present study gives evidence that especially in cancer treatment intra-tumoral injections will result in more efficient elimination of the tumor. The observation that monocyte-derived IL-3/IFN-β DC are able to trigger apoptosis in tumor cells is relevant to their therapeutic use as anti-tumor vaccines. Indeed, recent reports demonstrated that human IL4/GM-CSF DC can process apoptotic cells and cross-present the derived antigens in a MHC-class I restricted fashion, resulting in the induction of efficient cytotoxic T cell responses. Therefore DC which are directly injected into tumors will first induce apoptosis of cancer cells, and finally migrate in the lymph nodes where they induce tumor-specific T-cell responses.

These compositions may, for example, be administered parenterally or intravenously. The compositions according to the invention for parenteral administration can be, in particular, sterile solutions, aqueous or non-aqueous, suspensions or emulsions. As a pharmaceutically acceptable solution or vehicle propylene glycol, polyethylene glycol, injectable organic esters, for example ethyl oleate, or cyclodextrins may be employed.

These compositions can also comprise wetting, emulsifying and/or dispersing agents.

The sterilisation may be carried out in several ways, for example, using bacteriological filter, by incorporating sterilising agents in the composition or by irradiation. They may also be prepared in the form of sterile solid compositions which may be dissolved at the time of use in sterile water or any other sterile injectable medium.

The present invention can also comprise adjuvants which are well known to a person skilled in the art (vitamin C, antioxidant agents, etc.) capable of being used in synergy with the compounds according to the invention in order to improve and prolong the treatments of cancerous tumors.

The invention also relates to a composition comprising a composition according to present invention and another compound as a combined preparation for simultaneous, separate or sequential use for treating cancer, infections and autoimmune diseases.

The present invention also relates to a method for the preparation of a composition as described by present invention comprising following steps:
(a) isolating monocytes from a patient,
(b) incubating said monocytes in a closed system in the presence of clinical grade IFN-β and IL-3 to provide a population of IL3-R+ CD11c+ myeloid dendritc cells,
(c) presenting an antigen on the surface of said dendritic cells in clinical grade conditions, thereby providing a population of antigen presenting dendritic cells; and,
(d) activating a population of T cells with said population of antigen presenting dendritic cells, whereby said IL3-R+ CD11c+ myeloid dendritic cells are unstimulated or stimulated using a method according to present invention, or a combination thereof.

As described above each of these steps can be performed in vitro and/or in vivo.

Recently improvements were made for the production of DC in clinical-grade conditions. The present inventors described in Toungouz et al 1999[46] that the development of closed systems, avoidance of exogenous proteins and respect of standard operating procedures (SOP) is needed to be able to guarantee predefined specifications of the cellular product. In these documents a good manufacturing practice (GMP)-simplified procedure of IL4/GM-CSF DC generation from leukapheresis products in a closed system, using synthetic culture media devoid of non-human protein is described. In analogy to this method, clinical grade IL-3/IFN-β DC can be prepared.

Unless otherwise defined, all technical and scientific terms used herein have the same meaning as commonly understood by one of ordinary skill in the art to which this invention belongs. Exemplary methods and materials are described below, although methods and materials similar or equivalent to those described herein can be used in the practice or testing of the present invention. All publications and other references mentioned herein are incorporated by reference in their entirety. In case of conflict, the present specification, including definitions, will control. The materials, methods, and examples are illustrative only and not intend to be limiting. Other features and advantages of the invention will be apparent from the following drawings, tables, detailed description, and from the claims.

BRIEF DESCRIPTION OF THE FIGURES AND TABLES

FIG. 1. IFN-β prevents IL-3Rα downregulation on cultured monocytes

Monocytes incubated in medium alone or with IFN-β (1000 U/ml) were analyzed by flow cytometry for the expression of IL-3Rα (CD123). Thick line: FACS profiles after staining with PE-conjugated anti-CD123 antibodies. Dotted lines: FACS profiles after staining with isotype-matched control IgG1. Data from one representative experiment out of 3 on different blood donors.

Figure 2:
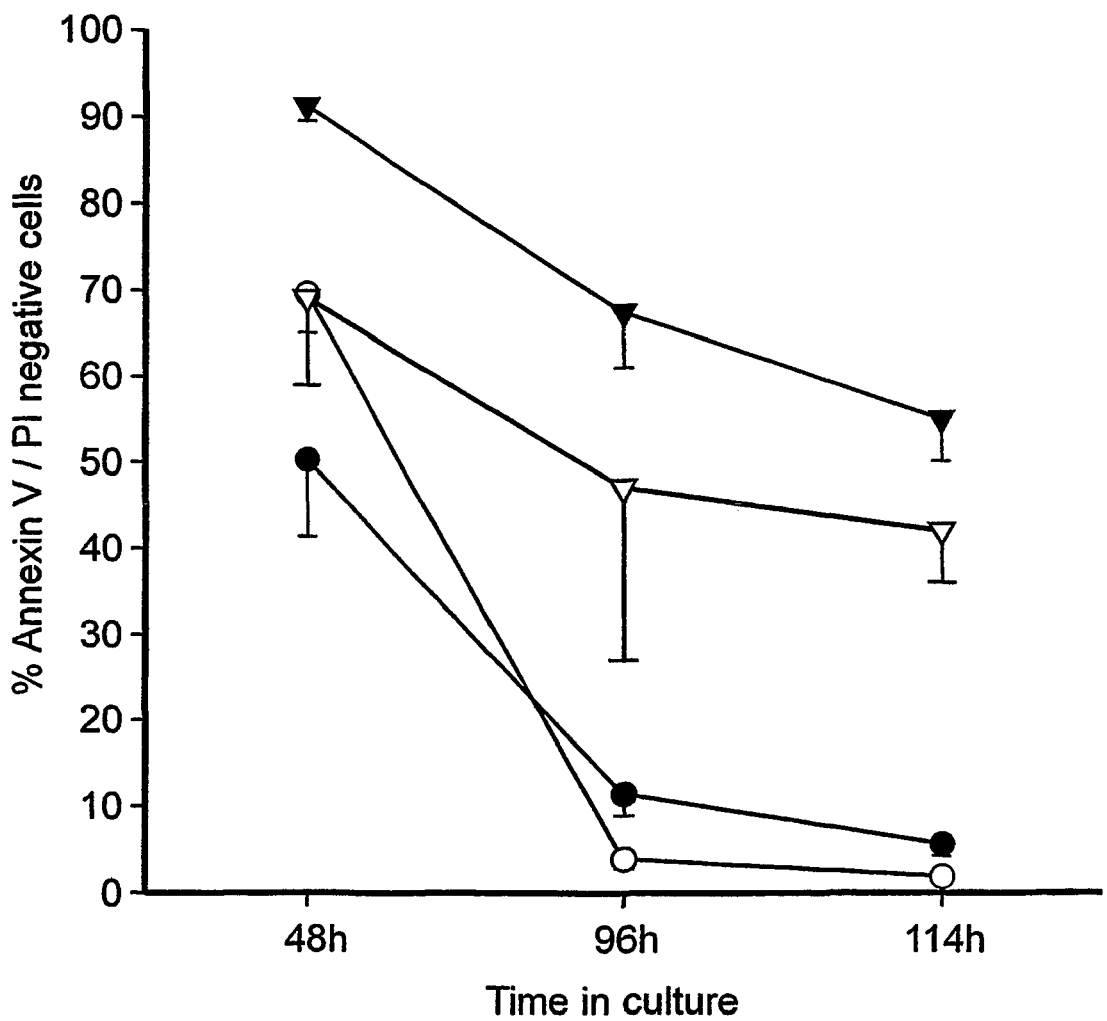

FIG. 2. IFN-β cooperate with IL-3 to promote monocyte survival

Monocytes were cultured in medium alone (○), or in the presence of 50 U/mi IL-3 (▽), or 1000 U/ml IFN-β (●) or a combination of 1000 U/ml IFN-β and 50 U/ml IL-3 (▼). Apoptotic cells were enumerated by flow cytometry after staining for annexin V and propidium iodide (PI). Results were expressed as mean±SEM of percentages of cells negative for the expression of both annexin V and PI.

Figure 3:
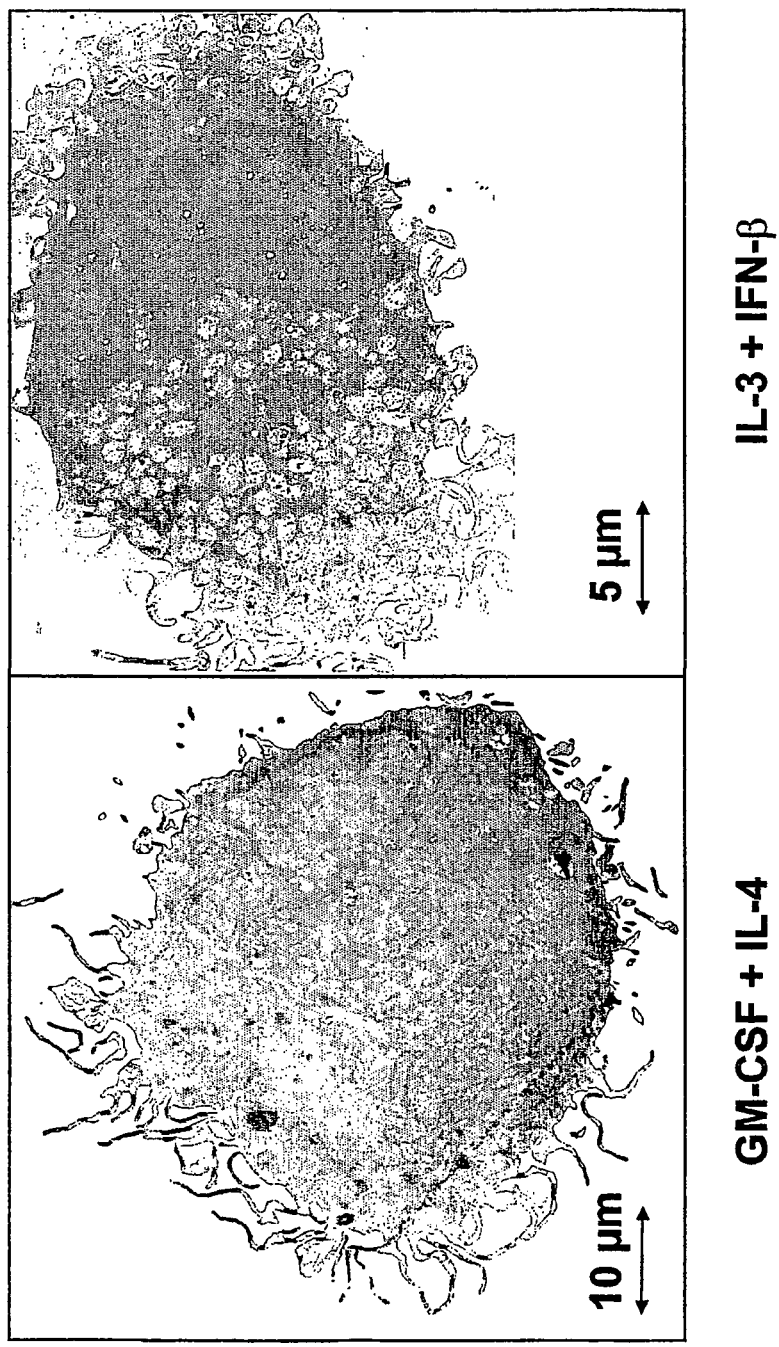

FIG. 3. Ultrastructure of cells derived from monocytes cultured in the presence of IFN-β and IL-3

Transmission electron microscopy of monocytes after culture for 6 days with either GM-CSF and IL4 or IL-3 and IFN-β (original magnification A ; ×900, B ; ×1950). Both IL-3/IFN-β DC and GM-CSF/IL4 DC showed typical appearance of dendritic cells including a lobulated nucleus, long cytoplasmic processes and tubulovesicular system. In the presence of IL-3 and IFN-β, DC appeared as smaller cells filled with mitochondria.

FIG. 4. Expression of surface markers on cells derived from monocytes cultured in IL-3 and IFN-β

(A) Phenotype of purified monocytes cultured for 6 days with either GM-CSF and IL-4 or IL-3 and IFN-β. Thick line:

FACS profiles after staining with specific antibodies. Dotted lines: FACS profiles after staining with isotype-matched control antibodies. Data from one representative experiment out of 6 on different blood donors.

(B) Phenotype of purified monocytes cultured with GM-CSF and IL-4, or IL-3 and IFN-β or IL-3 alone. Thick line: FACS profiles after staining with specific antibodies. Thin lines: FACS profiles after staining with isotype-matched control antibodies. Data from one representative experiment out of 6 on different blood donors.

FIG. 5. Expression of surface markers on cells derived from monocytes cultured in IL-3 and IFN-α

Phenotype of monocytes cultured with either IL-3 and IFN-β or with IL-3 and IFN-α. Thick lines: FACS profiles after staining with specific antibodies. Thin lines: FACS profiles after staining with isotype-matched control antibodies.

Figure 6:
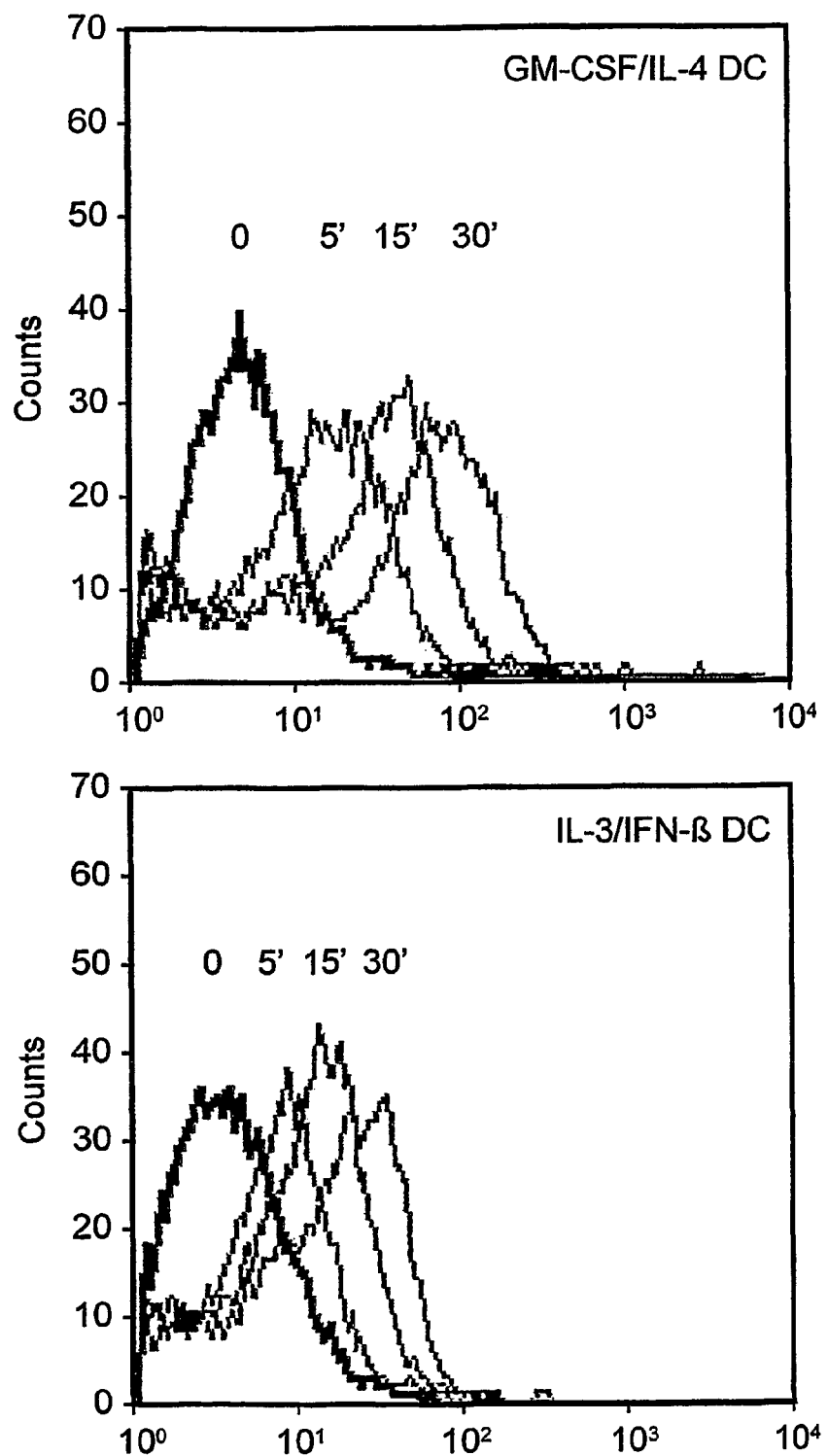

FIG. 6. Internalization of FITC-Dextran in IL-3/IFN-β DC

DC grown in GM-CSF and IL4 or in IL-3 and IFN-β were incubated in medium containing 1 mg/ml FITC-Dextran for the indicated times and analyzed by flow cytometry. Results are from one representative experiment out of 3 on different blood donors.

Figure 7:
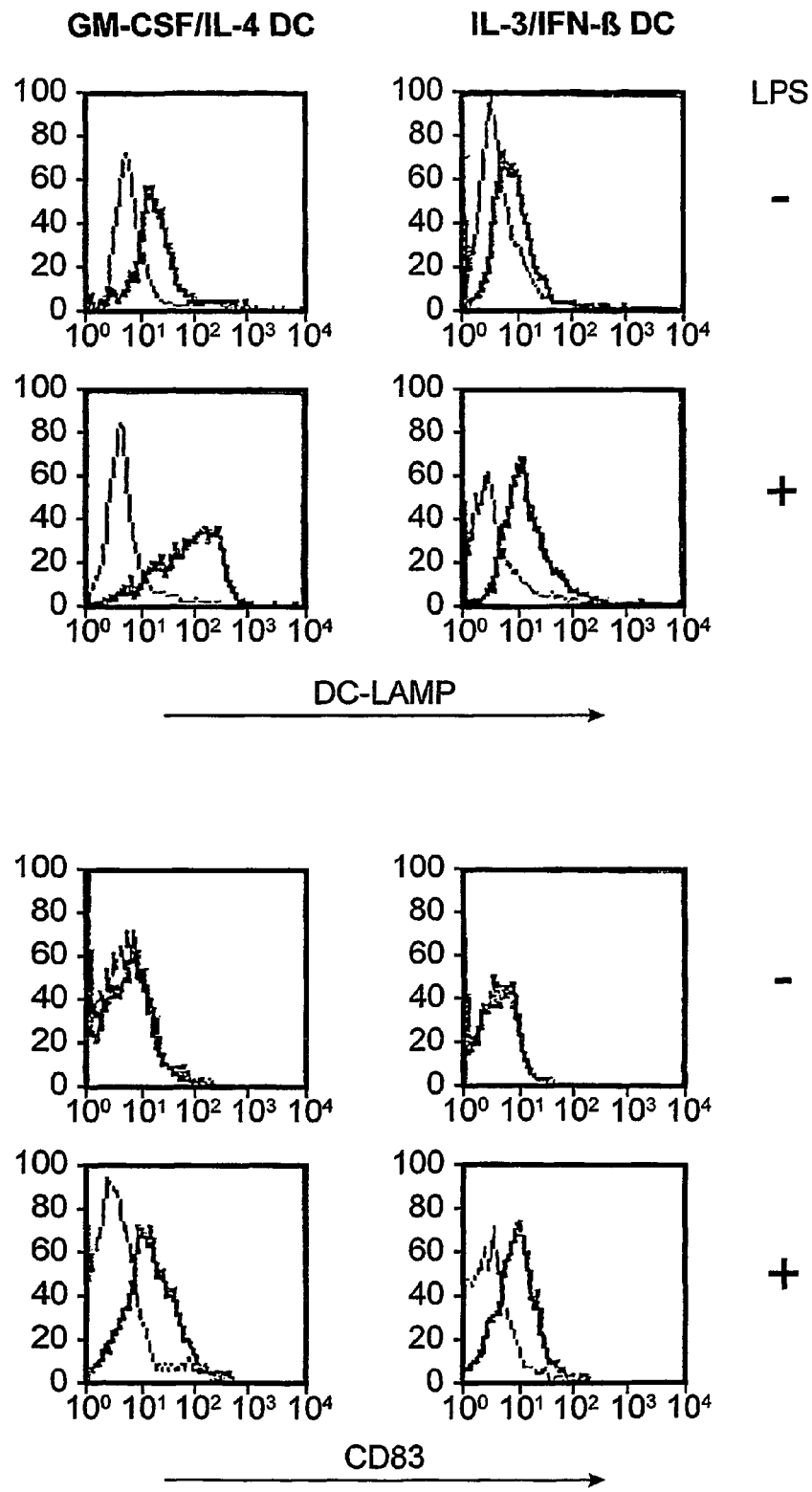

FIG. 7. DC-LAMP and CD83 are expressed on LPS-stimulated IL-3/IFN-β DC

Monocytes were cultured with either GM-CSF and IL-4 or IL-3 and IFN-β. DC were then stimulated or not with LPS (1 µg/ml) for 24 h. Thick lines: FACS profiles after staining with specific antibodies. Thin lines: FACS profiles after staining with isotype-matched control antibodies. Data from one representative experiment out of 2 on different blood donors.

FIG. 8. T cell stimulatory activity of IL-3/IFN-β DC (A) IL-3/IFN-β DC induce proliferation of naive $CD4^+$ T cells. Cord blood $CD4^+$ T cells were cultured with allogenic IL-3/IFN-β DC (O) or GM-CSF/IL-4 DC (●) prepared from the same donors. After 5 days, T cell proliferation was quantified by [$^3$H] thymidine incorporation. Data are shown as means±SEM of 6 independent experiments.

(B) Production of cytokines in mixed leucocyte cultures. Peripheral blood $CD4^+$ T cells were cultured with allogenic IL-3/IFN-β DC (hatched columns) or GM-CSF/IL-4 DC (open colums) at a DC:T ratio of 1:10. After 6 days, culture supernatants were assayed by ELISA for determination of cytokine levels. Data are shown as mean±SEM of 6 experiments.

*$p<0.05$ as compared to DC generated in GM-CSF and IL-4 (Wilcoxon's test).

Figure 9:
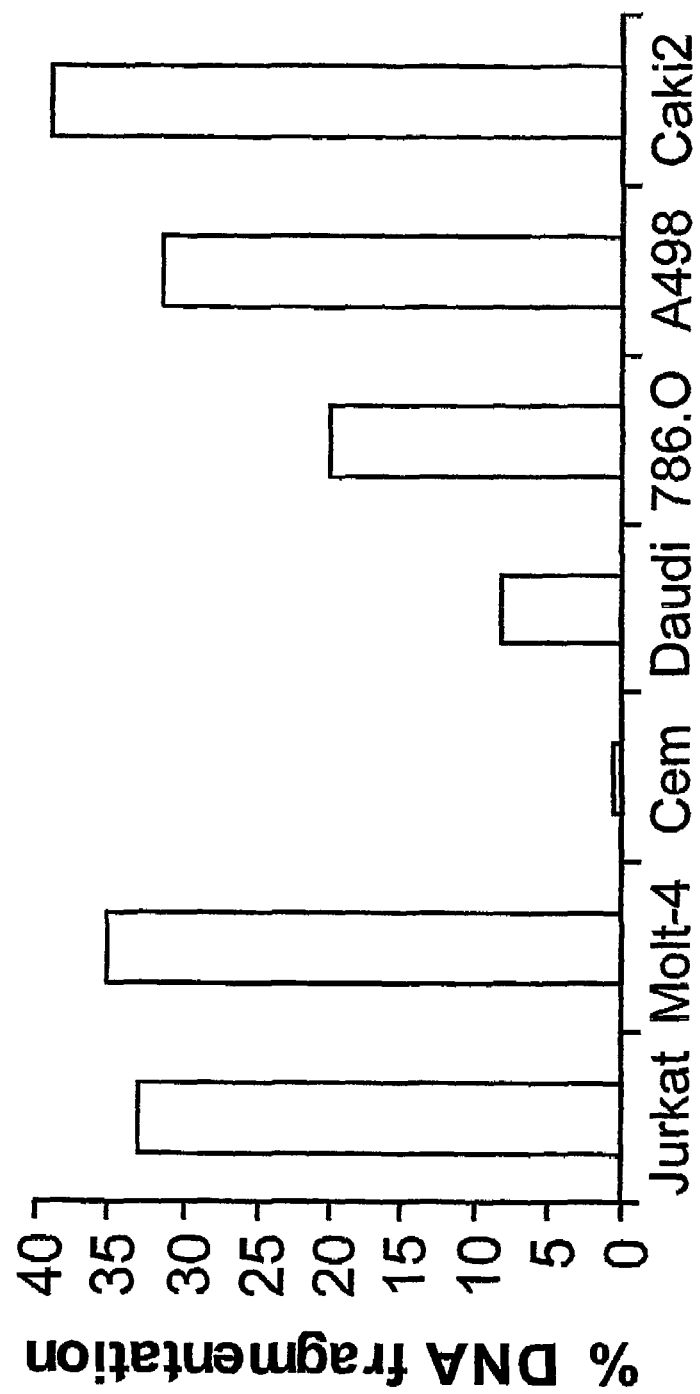

FIG. 9. Apoptosis of cancer cells using IL-3/IFN-β DC.

Human monocyte-derived DC generated from monocytes cultured in IL-3 and IFN-β were cocultured with [3H] thymidine-labeled tumor cell lines. After 18 h, intact nuclei were harvested and radioactivity was measured. Data are expressed as percentages of DNA fragmentation at 10:1 DC:target cell ratio.

Figure 10:
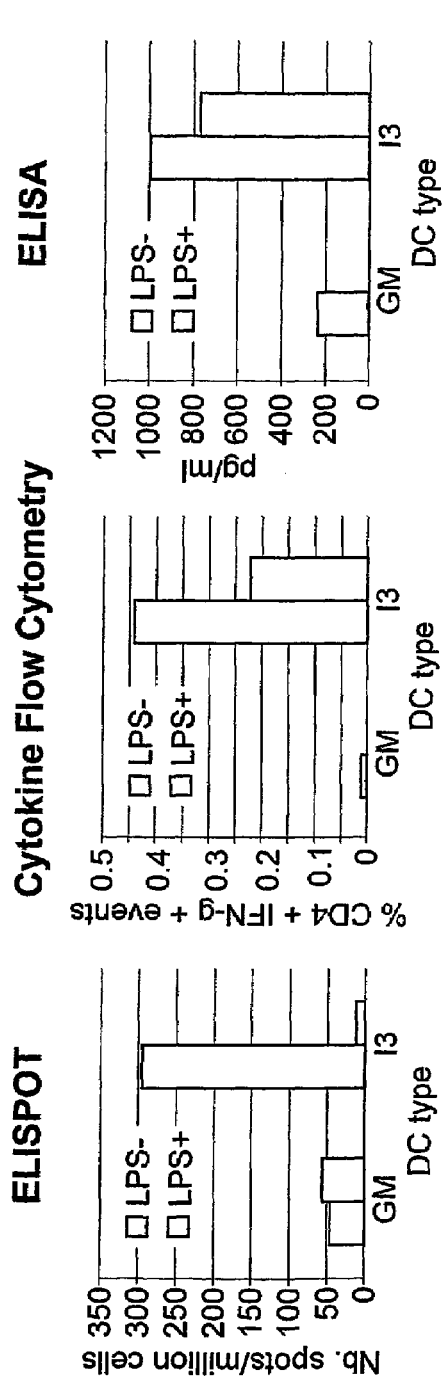

FIG. 10. ANTI-E7 response induced by IFN-β/IL-3 DC; as compared to GM-CSF/IL-4 DC Anti E7 IFN-g response induced by 13 DC as compared to GM DC. Light bars represent response obtained with unstimulated DC whereas dark bars represent responses induced with stimulated LPS stimulated DC. ELISPOT, ELISA and cytometry were used as read-out systems. Results plotted are those obtained after subtraction of the background (unloaded DC+ autologous T cells).

TABLE 1. CYTOKINE PRODUCTION BY MONOCYTE-DERIVED DC

DC were generated in presence of either GM-CSF and IL-4 or IL-3 and IFN-β and activated with LPS (1 µg/ml) for 24 h or with 3T6-CD40L transfectants for 3 days. Cytokine levels in supernatants were measured by ELISA and results were expressed as means±SEM of 6 independent experiments on different blood donors.

TABLE 2. Poly (I:C) Induces IFN-α Production by IL-3/IFN-β DC

DC were generated in presence of IL-3 and IFN-β, and activated either with 3T6-CD40L transfectants for 3 days, or LPS (1 µg/ml) for 24h, or Influenza virus for 24 h or Poly (I:C) for 48 h. IFN-α levels in supernatants were measured by ELISA and results were expressed as means±SEM of independent experiments on different blood donors.

EXAMPLES

Example 1

Interleukin-3 and Interferon-β Cooperate to Induce Differentiation of Monocytes into Dendritic Cells with Potent Helper T Cell Stimulatory Properties Materials and Methods Cell Preparation and Culture Peripheral blood mononuclear cells (PBMC) were obtained from heparinized blood of normal donors by centrifugation over Lymphoprep density gradient (Nycomed, Oslo, Norway). Monocytes were obtained either by 2h adhesion in 75 $cm^2$ flasks or by centrifugation over Nycoprep density gradient (Nycomed), following by magnetic cell sorting using a commercially available monocyte isolation kit allowing to obtain cell suspensions containing more than 95% monocytes (Miltenyi Biotec, Auburn, Calif.). To generate DC using IL-4 and GM-CSF (IL4/GM-CSF DC), purified monocytes were cultured for 46 days in RPMI 1640 (Bio Whittaker Europe, Verviers, Belgium) supplemented with 2 mM L-glutamine (GIBCO, Paisley, Scotland), 20 µg/ml gentamicin, 50 µM 2-mercaptoethanol (GIBCO), 1% non-essential amino acids (GIBCO) and 10% fetal bovine serum (Bio Whittaker Europe) in 75 $cm^2$ flasks or 6 well plates (7.5 $10^5$ cells/ml) in the presence of GM-CSF (800 U/ml) and IL4 (500 U/ml) kindly provided by Schering-Plough (Kenilworth, N.J.), as described by Romani et al.[4]. In parallel, monocytes were cultured for 4-6 days in presence of IFN-β (1000 U/ml) (Ares Serono Europe, London, UK) and IL-3 (50 U/ml) (R&D Systems Europe, Oxon, UK), alone or in combination.

Electron Microscopy Study

Dendritic cells were fixed with 2% glutaraldehyde and Millonig's phosphate buffer for 2 h. Cell blocks obtained after 1200 g centrifugation for 10 min were postfixed with 2% osmium tetroxide and embedded in epoxy resin. Ultra-thin sections were stained with uranyl-acetate and lead citrate. Ultrastructural study was performed using the electron microscope EMT400 (Philips, Eindhoven, Holland).

Flow Cytometry Analysis

For immunophenotyping, cells were washed in phosphate buffered saline (PBS) supplemented with 0.5% bovine serum albumin (BSA) and incubated for 15 min at 4° C. with one of the following fluoresceinated (FITC-) or phycoerythrin (PE)-conjugated monoclonal antibodies: FITC-anti-HLA-DR IgG2a, PE-anti-CD4 IgG1, FITC-anti-CD8 IgG1, PE-anti-CD11b IgG2a, PE-anti-CD11c IgG2b, PE-anti-CD14 IgG2b, PE-anti-CD33 IgG1, FITC-anti-CD45RA IgG1, PE-anti-CD45RO IgG2a, PE-anti-CD54 IgG2b, PE-anti-CD80 (B7-1) IgG1, PE-anti-CD123 (IL-3Rα) IgG1 and PE-anti-CD154 (CD40L) $IgG_1$, all from Becton Dickinson (Mountain View, Calif.), PE-anti-CD86 (B7-2) IgG2b from Pharmingen (San Diego, Calif.), FITC-anti-CD3 IgG2a, FITC-anti-CD16 IgG1, FITC-anti-CD19 IgG1 and PE-anti-CD40 IgG1 from Biosource International (Camarillo, Calif.), FITC-anti-CD1a IgG2a from Dako (Glostrup, Denmark), and FITC-anti-HLA-Class I (A,B,C) clone B9.12.1 IgG2a, PE-anti-CD83 IgG2b from Immunotech (Marseille, France). Cells were also stained with corresponding isotype-matched control monoclonal antibodies and then analyzed using a FACScan flow cytometer (Becton Dickinson).

Apoptosis Analysis

Apoptotic cell death was measured by flow cytometry using FITC-conjugated annexin V (Becton Dikinson) and propidium iodide (Sigma-Aldrich, Bornem, Belgium) as per the manufacturer's protocol.

Endocytosis Assay

FITC-dextran (Molecular Probes, Eugen, Oreg.) was used to assess cell endocytosis as described by Sallusto et al.[17]. Briefly, cells were incubated with 1 mg/ml FITC-dextran at 37° C. for 5, 15 or 30 min and then analyzed using the FACScan flow cytometer.

Dendritic Cell Stimulation

DC ($4 \times 10^5$/ml) were stimulated by bacterial lipopolysaccharide (LPS) (1 µg/ml), formaldehyde-inactivated influenza virus strain New Caledonia (kindly provided by N. Kuehm, Aventis, Pasteur Mérieux, Val de Reuil, France), or Polyinosinic-polycytidylic acid (Poly (I:C) (20 µg/ml) (Sigma), for 24 h or 48 h respectively, and culture supernatants were then assayed for cytokine levels. In parallel, DC ($2 \times 10^5$/ml) were activated by co-culture with irradiated 3T6 fibroblasts transfected with the human CD40L gene (CD40L transfectants) ($5 \times 10^4$/ml), and supernatants were harvested after 3 days for determination of cytokine levels.

Mixed Leucocyte Cultures

DC were co-cultured in 96-well flat-bottom plates with allogenic naive CD4$^+$ T cells ($2 \times 10^5$/ml) isolated from newborn cord blood or adult PBMC. CD4$^+$ T cells were purified by magnetic cell sorting using a commercially available CD4 T cell isolation kit (>95% purity as assessed by FACS analysis) (Miltenyi Biotec). In the case of adult CD4+ T cells, a CD45RA isolation kit (Miltenyi Biotec) is further used for the enrichment in naive cells.

After 5 days, cell proliferation was assessed by [3H] thymidine uptake during the last 16h and culture supernatants were collected for determination of cytokine levels.

Determination of Cytokine Levels

ELISA kits were purchased from Biosource Europe (Fleurus, Belgium) for determination of TNFα, IL-6, IL-8 and IL-12 (p40) levels. Determination of IL-12 (p70) levels was performed using a commercially available kit (Endogen, Woburn, Mass.). IFN-γ and IL-5 levels were measured by two-site sandwich ELISA using antibodies from Chromogenix (Mölndal, Sweden) and Pharmingen, respectively.

Statistical Analysis

Statistical Significance was Determined Using Two-tailed Paired Wilcoxon's Test.

Results

IFN-β-treated monocytes maintain IL-3Rα expression and depend on IL-3 for their survival As shown in FIG. 1 monocytes purified from PBMC express IL-3Rα (CD123) but lose this expression after 6 days of culture in medium alone. The loss of IL-3Rα expression was prevented when IFN-β (1000 IU/ml) was added on the first day of culture (FIG. 1). This analysis was performed on the fraction of viable cells in the culture. Indeed, more than 90% of monocytes cultured in medium alone or in presence of 1000 IU/ml IFN-β were apoptotic, as assessed by flow cytometry using double staining with annexin-V and propidium iodide (FIG. 2). The addition of IL-3 on the first day of culture dramatically enhanced monocyte survival. Indeed, more than 65% of cells were still alive after 6 days of culture in presence of IL-3 and IFN-β.

Monocytes Cultured in Presence of IL-3 and IFN-β Differentiate into DC

To characterize the cells obtained by culture of monocytes in IL-3 and IFN-β, the inventors first looked at their ultrastructural morphology. As shown in FIG. 3, monocytes cultured under this condition acquired cytoplasmic expansions of the dendritic type. Cells derived from monocytes cultured in IL-3 and IFN-β will therefore be referred hereafter as IL-3/IFN-β DC.

Flow cytometry analysis (FIG. 4) demonstrated that these cells expressed markers of the myeloid lineage (CD11c, CD14, and CD33) but were negative for the surface expression of CD3, CD4, CD8, CD11b, CD16, CD19, CD45RA and CD154 (CD40L). They also expressed high levels of HLA class I and class II molecules, CD40, CD54, CD 80 and CD86, and IL-3Rα (CD123). As expected[7], the latter marker was expressed at only low level on DC derived from monocytes cultured in IL-4 and GM-CSF. Conversely, CD1a was expressed on IL-4/GM-CSF DC but not on cells derived from monocytes cultured in IL-3 and IFN-β.

When monocytes were cultured in IL-3 alone, they strongly adhered to plastic, so that only limited numbers of such cells could be collected for further analysis. By flow cytometry, they expressed lower levels of CD80 and CD86 and higher levels of CD14 than IL-3/IFN-β DC (FIG. 4), which suggests that they are more close to macrophages. In additional experiments, the inventors found that IFN-α exerts a similar effect as IFN-β, as the IL-3+IFN-α combination also resulted in the generation of myeloid IL-3Rα-positive DC expressing CD80 and CD86 (FIG. 5).

The endocytosis capacity of IL-3/IFN-β DC was studied by fluid phase uptake of FITC-dextran. As shown in FIG. 6, IL-3/IFN-β DC actively engulf dextran, although they were less potent than IL4/GM-CSF DC in doing so.

To further study the maturation status of IL-3/IFN-β DC, the inventors analyzed their expression of CD83 and DC-LAMP which are established markers of mature DC. As shown in FIG. 6, both markers were absent on resting IL-3/IFN-β DC but were clearly upregulated upon LPS stimulation (FIG. 7).

Production of Cytokines by IL-3/IFN-β DC

IL-3/IFN-β DC spontaneously secreted IL-6, IL-8, IL-12 (p40) and TNFα. As compared to GM-CSF/IL-4 DC, IL-3/IFN-β DC produced less IL-12 (p40) whereas their secretion of IL-8 was slightly higher (table 1). As it is the case for IL-4/GM-CSF DC, both LPS and CD40 ligation induced by CD40L transfectants upregulated the synthesis of cytokines by IL-3/IFNβ DC. As compared to GM-CSF/IL-4 DC, IL-3/IFN-β DC produced lower levels of TNF-α in response to LPS, higher levels of IL-6 and IL-8 in response to CD40L, and much lower levels of IL-12 (p40) and IL-12 (p70) regardless the stimulus considered.

To analyze the production of IFN-α, the inventors included as additional stimuli formaldehyde-inactivated influenza virus and Poly (I:C) which mimicks viral double-stranded RNA. As shown in table 2, Poly (I:C) was the only stimulus inducing IFN-α production by IL-3/IFN-β DC. Under this condition, IFN-α levels secreted strongly by IL-3/IFN-β DC were more than ten-fold higher that those produced by IL-4/GM-CSF DC (128±24 pg/ml, p<0.05) (FIG. 12).

T Cell Activation Induced by IL-3/IFN-β DC

To evaluate the ability of IL-3/IFN-β DC to elicit naive T cell responses, mixed leucocyte cultures were prepared between cord blood CD4+ T cells and either IL-4/GM-CSF or IL-3/IFN-β DC. At all stimulator/responder ratios, IL-3/IFN-β DC were as efficient as GM-CSF/IL-4 DC to induce naive CD4+ T cell proliferation (FIG. 8A). In subsequent experiments designed to analyze the profile of cytokines secreted by T cells upon exposure to allogenic DC, mixed lymphocyte cultures were prepared using adult CD45RA+ CD4+ T cells as responder cells. As shown in FIG. 8B, IL-3/IFN-β DC induced the production of large amounts of IFN-γ much higher than to those elicited by IL-4/GM-CSF DC. To determine whether IL-12 was involved in the induction of IFN-γ production, the inventors added a neutralizing anti-IL-12 antibody to the mixed leucocyte cultures. IL-12 neutralization inhibits more than 60% of the IFN-γ production whatever the DC type considered (data not shown), indicating that the low levels of IL-12 secreted by IL-3/IFN-β DC contribute to their ability to elicit IFN-γ production by T cells. Likewise, IL-3/IFN-β DC also induced IL-5 production in mixed leucocyte culture and were also much more efficient than IL-4/GM-CSF DC in that respect (FIG. 8B).

Discussion

Among DC population, distinct lineages were defined according to the expression of surface molecules. CD11c+ CD123− DC display feature of myeloid lineage and depend on GM-CSF for their survival[5;18], The IL-3-dependent CD11c− CD123+ DC are thought to belong to lymphoid lineage[7] although Olweus et al. showed that in the T cell-dependent areas of human lymphoid organs, a large subset of DC expressing high levels of IL-3Rα belong to a myeloid lineage[19]. The experiments described by the inventors demonstrate that monocytes cultured in IL-3 and IFN-β give rise to a distinct type of DC expressing high level of both CD11c and CD123 surface molecules. In addition to their morphology, their dendritic cell nature was further established by their capacity to induce proliferation of naive CD4+ T cells in MLR. Interestingly, IL-3 was previously shown to cooperate with tumor necrosis factor in the generation of dendritic/Langerhans cells from CD34+ hematopoietic progenitor cells[20]. As the starting population in the experiments, performed by the inventors, consists of purified monocytes and the IL-3/IFN-β DC differ from the dendritic/Langerhans cells in terms of CD1a and CD14 expression, it appears that IL-3 can promote differentiation of distinct DC populations.

Recently, IFN-β have been shown able to enhance maturation of monocyte-derived DC[21]. As compared to classical DC generated in GM-CSF and IL-4, IL-3/IFN-β DC are at a higher stage of maturation, as indicated by their increased surface expression of costimulatory and HLA molecules. Decreased endocytic capacity of IL-3/IFN-β DC may also reflect their higher maturation level[22]. As far as cytokine production is concerned, IL-3/IFN-β DC secrete much lower level of IL-12 as compared to GM-CSF/IL-4 DC. This could be related to their higher stage of maturation, as DC maturation was previously shown to result in a lower production of IL-12[23]. Moreover, IFN-β might directly inhibit IL-12 synthesis by DC[24]. The fact that IL-3/IFN-β DC exhibited less endocytosis capacity may also reflect their higher maturation level. Although displaying several features suggestive of a higher degree of maturation than IL-4/GM-CSF DC, IL-3/IFN-β DC should not be considered as fully mature as they do not express CD83 and DC-LAMP. However, these markers clearly appeared upon LPS stimulation as in the case of IL-4/GM-CSF DC.

A previous study observed that DC differentiated from monocytes cultured in presence of IFN-β and GM-CSF are short-lived[16]. In this report, the present inventors demonstrate that IL-3 rescue monocytes cultured in presence of IFN-β from apoptosis, and allow them to differentiate into mature DC. These observations demonstrate a cooperating effect of IL-3 and IFN-β on cell survival and differentiation. Little is known on the effect of both type I and type II IFNs on IL-3 receptor expression. The effect of type I IFNs on IL-3Rα expression has never been assessed, but IFN-γ proved to upregulate IL-3Rα expression in human endothelial cells[25]. Moreover, IFN-γ has been shown to have a synergistic effect with IL-3 on the growth of immature human hematopoietic progenitors[26], though this effect was not correlated with upregulation of IL-3Rα expression[27]. Nevertheless, IL-3 is well known to stimulate monocyte differentiation from myeloid progenitors and their activation[28-30]. More recently, IL-3 proved to be a critical survival factor for IL-3Rα precursors of DC isolated from human blood, lymph nodes and bone marrow[6;7;19].

Despite their low level of IL-12 production, IL-3/IFN-β DC stimulate high level of IFN-γ production from adult CD4+ T cells, suggesting that they use other factors or membrane molecules to elicit the synthesis of Th1 cytokines. Indeed IL-12 independent pathway of IFN-γ were recently described[13;14;31-33]. However, the reduced IFN-γ levels measured upon IL-12 neutralization indicate that IL-12 contributes to the function of IL-3/IFN-β DC. Taken together, the data as presented in present invention indicated that IL-3/IFN-β DC differ from the CD4+ CD3− CD11c− IL-3Rα+ plasmacytoid cells isolated from peripheral blood described by Grouard et al.[6], as the latter cells proved to be poor inducers of IFN-γ in MLR.

The capacity of IL-3/IFN-β DC to produce high levels of IFN-α upon Poly I:C stimulation might be relevant to their effects in the setting of viral infections[34]. This response to Poly I:C is consistent with their myeloid origin[35]. Interestingly, IL-3/IFN-β DC respond low to influenza virus in relation with the induction of MxA by IFN-β[36]. The differential responsiveness to influenza virus and Poly (I:C) is consistent with the fact that Poly (I:C) acts on the protein kinase R expressed in the cytoplasm whereas surface receptors are involved in responses to whole viruses[37].

Monocyte-derived IL-4/GM-CSF DC are now used clinically as tools to induce antitumor immunity[338-40]. Herein, the inventors show that IL-3/IFN-β DC are more efficient than IL-4/GM-CSF to elicit IFN-γ and IL-5 production by helper T cells. This might be relevant to cancer vaccination as both cytokines were found to synergize in tumor rejection[41]. Because of their ability to induce the production of both IFN-γ and IL-5 and their easy generation from peripheral blood monocytes, the inventors suggest that IFN-β/IL-3 DC might be of interest for the development of new cancer therapies based on DC.

Summary of Example 1

The inventors observed that interferon-β (IFN-β) prevented the down-regulation of the interleukin-3 receptor a chain (IL-3Rα) which spontaneously occurs during culture of human monocytes. The functionality of the IL-3R was demonstrated by the fact that IL-3 rescued IFN-β-treated monocytes from apoptosis. Whereas more than 90% monocytes died after 6 days of culture in IFN-β alone, 65% of cells were still alive in presence of IL-3 and IFN-β. The inventors then found that monocytes cultured in presence of IFN-β and IL-3 acquire a dendritic morphology and express high levels of HLA class I and class II and costimulatory molecules such as CD40, CD54, CD80 and CD86. When stimulated by either lipopolysaccharide (LPS) or fibroblasts expressing CD40 ligand (CD40L transfectants), DC generated in IFN-β and IL-3 (IL-3/IFN-β DC) secreted high levels of IL-6, IL-8 and tumor necrosis factor (TNF)-α, but only very low levels of IL-12 in comparison with DC generated in IL-4 and granulocyte-macrophage colony-stimulating factor (IL-4/GM-CSF DC). The inventors found that IL-3/IFN-β DC induced a vigorous proliferative response of allogenic cord blood T cells. In mixed leucocyte culture with adult $CD4^+$ T cells, IL-3/IFN-β DC elicited the production of high levels of both IFN-γ levels and IL-5. Finally, IL-3/IFN-β DC were found to produce much higher levels of IFN-α than IL-4/GM-CSF DC in response to Poly (I:C). The inventors conclude that monocytes cultured in presence of IL-3 and IFN-β differentiate into DC with potent helper T cell stimulatory capacity despite their low expression of IL-12.

Example 2

Human Monocyte-derived Dendritic Cells Generated in IL-3 and IFN-β Induce Apoptosis of Tumor Cell Lines It was proven by the inventors that human monocyte-derived DC generated from periferal blood mononuclear cells by culture in interleukin (IL)3 and interferon(IFN)-β (IL-3/IFN-β DC) may be used in clinical trials as tool to induce anti-tumor responses in vivo[38-40]. In order to determine whether IL-3/IFN-β DC are able to induce programmed cell death in tumor cells, those cells were co-cultured with a panel of tumor cell lines (Jurkat cell line, the Molt-4 cell line (obtained from the Institut Pasteur, Lille, France); Cem cell line (obtained fron Dr. T. Velu (ULB, Brussels, Belgium), 786.0, A498 and Caki 2 cell lines provided by Dr. R. Kiss (ULB, Bussels, Belgium);Daudi cell lines purchased from ATCC). The percentage of DNA fragmentation into target cells was measured using the jam test. Briefly, target cells were labeled with 5 µCi/ml of [$^3$H] thymidine by overnight incubation at 37° C. Labeled target cells were harvested, washed and seeded in 96 well U-bottom plates at a density of 10,000 cells/well. Effector cells were washed and added to the target cells. After 18 h, intact nuclei (unfragmented high M.W. DNA) were harvested using a micro 96 harvester and radioactivity was measured on a micro plate beta counter. Data were expressed as percentage of DNA fragmentation calculated by the following formula: [1-(cpm with effector/cpm without effector)]×100. The present inventors observed that IL-3/IFN-β DC at a ratio of E:T=10:1 exhibit significant cytotoxic activity against 6 out 8 tested tumor lines. As shown in FIG. 9, Molt-4, Jurkat, 786.0, A498 and Caki2 cell lines were susceptible to IL-3/IFN-β DC-mediated apoptosis, as well as Daudi cells although to a lesser extent. On the other hand, Cem cells were resistant.

The observation that monocyte-derived IL-3/IFN-β DC are able to trigger apoptosis in tumor cells is relevant to their therapeutic use as anti-tumor vaccines. Indeed, recent reports demonstrated that human IL-4/GM-CSF DC can process apoptotic cells and cross-present the derived antigens in a MHC-class I restricted fashion, resulting in the induction of efficient cytotoxic T cell responses[42-43]. Therefore DC which are directly injected into tumors will first induce apoptosis of cancer cells, and finally migrate in the lymph nodes where they induce tumor-specific T-cell responses.

Example 3

ANTI-E7 Response Induced by IFN-b/IL-3 DC as Compared to GM-CSF/IL-4 DC(FIG. 10)

Material and Methods

DC were generated from PBMCs of healthy blood donors by a 5 day culture in presence of either GM-CSF (800 IU/ml) and IL-4 (500 IU/ml) (GM DC or IL-4/CSF DC) or IL-3 (50 IU/ml) and IFN-β (1000 IU/ml) (I3 DC or IL3/IFN-β DC). After collection, these cells were pulsed for 2 hours with the E7 protein (20 µg/ml) at 370C in 5% CO2 atmosphere and activated or not with LPS (1 µg/ml, overnight stimulation). E7 pulsed DC were cocultured with autologous purified CD4+ T cells at a 1:10 ratio for 6 days. ELISPOT, ELISA and flow cytometry (intra-cellular staining) assessing IFN-γ production were used as read-out system.

Results

The data of these experiments show that non-activated I3 DC are at least equivalent or even superior to LPS stimulated GM DC for the induction of anti-E7 responses. As E7 is a protein derived from HPV 16, a virus involved in the pathogenesis of the cancer of the cervix, these data are relevant for the design of new cancer vaccines/immunotherapy.

REFERENCE

1. Banchereau J Steinman R M. Dendritic cells and the control of immunity. Nature. 1998;392:245-252.
2. Suss G Shortman K. A subclass of dendritic cells kills CD4 T cells via Fas/Fas-ligand-induced apoptosis. J Exp Med. 1996;183:1789-1796.
3. Caux C. Pathways of development of human dendritic cells. Eur J Dermatol. 1998;8:375-384.
4. Romani N, Reider D, Heuer M et al. Generation of mature dendritic cells from human blood. An improved method with special regard to clinical applicability. J Immunol Methods. 1996;196:137-151.
5. Sallusto F Lanzavecchia A. Efficient presentation of soluble antigen by cultured human dendritic cells is maintained by granulocyte/macrophage colony-stimulating factor plus interleukin 4 and downregulated by tumor necrosis factor alpha. J Exp Med. 1994;179:1109-1118.
6. Grouard G, Rissoan M C, Filgueira L et al. The enigmatic plasmacytoid T cells develop into dendritic cells with interleukin (IL)-3 and CD40-ligand. J Exp Med. 1997;185: 1101-1111.
7. Rissoan M C, Soumelis V, Kadowaki N et al. Reciprocal Control of T Helper Cell and Dendritic Cell Differentiation. Science. 1999;283:1183-1186.
8. Muller U, Steinhoff U, Reis L F et al. Functional role of type I and type II interferons in antiviral defense. Science. 1994;264:1918-1921.
9. Bogdan C. The function of type I interferons in antimicrobial immunity [In Process Citation]. Curr Opin Immunol 2000 August ;12 (4 ):419-24.12:419-424.
10. Belardelli F Gresser I. The neglected role of type I interferon in the T-cell response: implications for its clinical use. Immunol Today. 1996;17:369-372.
11. Biron C A. Activation and function of natural killer cell responses during viral infections. Curr Opin Immunol. 1997;9:24-34.
12. Siegal F P, Kadowaki N, Shodell M et al. The nature of the principal type 1 interferon-producing cells in human blood [see comments]. Science. 1999;284:1835-1837.

13. Celia M, Jarrossay D, Facchetti F et al. Plasmacytoid monocytes migrate to inflamed lymph nodes and produce large amounts of type I interferon [see comments]. Nat Med. 1999;5:919-923.
14. Kadowaki N, Antonenko S, Lau J Y, Liu Y J. Natural interferon alpha/beta-producing cells link innate and adaptive immunity. J Exp Med Jul. 17, 2000 ;192 (2 ):219 -26. 192:219-226.
15. Ito T, Amakawa R, Inaba M et al. Differential regulation of human blood dendritic cell subsets by IFNs. J Immunol. 2001;166:2961-2969.
16. Santini S M, Lapenta C, Logozzi M et al. Type I interferon as a powerful adjuvant for monocyte-derived dendritic cell development and activity in vitro and in Hu-PBL-SCID mice. J Exp Med May 15, 2000; 191 (10 ):1777 -88. 191: 1777-1788.
17. Sallusto F, Celia M, Danieli C, Lanzavecchia A. Dendritic cells use macropinocytosis and the mannose receptor to concentrate macromolecules in the major histocompatibility complex class II compartment: downregulation by cytokines and microbial products. J Exp Med. 1995;182: 389-400.
18. Romani N, Gruner S, Brang D et al. Proliferating dendritc cell progenitors in human blood. J Exp Med. 1994;180:83-93.
19. Olweus J, BitMansour A, Warnke R et al. Dendritic cell ontogeny: a human dendritic cell lineage of myeloid origin. Proc Natl Acad Sci U S A. 1997;94:12551-12556.
20. Caux C, Vanbervliet B, Massacrier C, Durand I, Banchereau J. Interleukin-3 cooperates with tumor necrosis factor alpha for the development of human dendritic/ Langerhans cells from cord blood CD34+ hematopoietic progenitor cells. Blood. 1996;87:2376-2385.
21. Luft T, Pang K C, Thomas E et al. Type I IFNs enhance the terminal differentiation of dendritic cells. J Immunol. 1998;161:1947-1953.
22. Celia M, Sallusto F, Lanzavecchia A. Origin, maturation and antigen presenting function of dendritic cells. Curr Opin Immunol. 1997;9:10-16.
23. Kalinski P, Schuitemaker J H, Hilkens C M, Wierenga E A, Kapsenberg M L. Final maturation of human dendritic cells is associated with decreased responsiveness to IFNγ and with resistance to bacterial IL-12 inducers:decreased ability of mature DC to produce IL-12 during the interaction with Th cells. The Journal of Immunology. 1999; 162:3231-3236.
24. McRae B L, Semnani R T, Hayes M P, van Seventer G A. Type I IFNs inhibit human dendritic cell IL-12 production and Th1 cell development. J Immunol. 1998;160:4298-4304.
25. Korpelainen E I, Gamble J R, Smith W B et al. Interferon-gamma upregulates interleukin-3 (IL-3) receptor expression in human endothelial cells and synergizes with IL-3 in stimulating major histocompatibility complex class II expression and cytokine production. Blood. 1995;86: 176-182.
26. Kawano Y, Takaue Y, Hirao A et al. Synergistic effect of recombinant interferon-gamma and interleukin-3 on the growth of immature human hematopoietic progenitors. Blood. 1991;77:2118-2121.
27. Sato N, Caux C, Kitamura T et al. Expression and factor-dependent modulation of the interleukin-3 receptor subunits on human hematopoietic cells. Blood. 1993;82:752-761.
28. Cavaillon J M. Cytokines and macrophages. Biomed Pharmacother. 1994;48:445-453.
29. Elliott M J, Vadas M A, Cleland L G, Gamble J R, Lopez A F. IL-3 and granulocyte-macrophage colony-stimulating factor stimulate two distinct phases of adhesion in human monocytes. J Immunol. 1990;145:167-176.
30. Lopez A F, Dyson P G, To L B et al. Recombinant human interleukin-3 stimulation of hematopoiesis in humans: loss of responsiveness with differentiation in the neutrophilic myeloid series. Blood. 1988;72: 1797-1804.
31. Rogge L, Barberis-Maino L, Biffi M et al. Selective expression of an interleukin-12 receptor component by human T helper 1 cells. J Exp Med. 1997;185:825-831.
32. Parronchi P, Mohapatra S, Sampognaro S et al. Effects of interferon-alpha on cytokine profile, T cell receptor repertoire and peptide reactivity of human allergen-specific T cells. Eur J Immunol. 1996;26:697-703.
33. Chapoval Al, Ni J, Lau J S et al. B7-H3: a costimulatory molecule for T cell activation and IFN-gamma production. Nat immunol. 2001;2:269-274.
34. Biron C A. Interferons alpha and beta as immune regulators--a new look. Immunity. 2001 ;14:661-664.
35. Kadowaki N. Antonenko S, Liu Y J. Distinct CpG DNA and polyinosinic-polycytidylic acid double-stranded RNA, respectively, stimulate CD11c-type 2 dendritic cell precursors and CD11c+ dendritic cells to produce type I IFN. J Immunol. 2001;166:2291-2295.
36. Celia M, Salio M, Sakakibara Y et al. Maturation, activation, and protection of dendritic cells induced by double-stranded RNA. J Exp Med. 1999;189:821-829.
37. Milone M C, Fitzgerald-Bocarsly P. The mannose receptor mediates induction of IFN-alpha in peripheral blood dendritic cells by enveloped RNA and DNA viruses. J Immunol. 1998;161:2391-2399.
38. Thurner B, Haendle I, Roder C et al. Vaccination with mage-3A1 peptide-pulsed mature, monocyte-derived dendritic cells expands specific cytotoxic T cells and induces regression of some metastases in advanced stage IV melanoma. J Exp Med. 1999; 190:1669-1678.
39. Schuler-Thurner B, Dieckmann D, Keikavoussi P et al. Mage-3 and influenza-matrix peptide-specific cytotoxic T cells are inducible in terminal stage HLA-A2.1+ melanoma patients by mature monocyte-derived dendritic cells [In Process Citation]. J Immunol Sep. 15, 2000; 165 (6 ):3492 -6.165:3492-3496.
40. Nestle F O, Alijagic S, Gilliet M et al. Vaccination of melanoma patients with peptide- or tumor lysate-pulsed dendritic cells [see comments]. Nat Med. 1998;4:328-332.
41. Hung K, Hayashi R. Lafond-Walker A et al. The central role of CD4(+) T cells in the antitumor immune response. J Exp Med. 1998;188:2357-2368.
42. Albert M L, Pearce S F, Francisco L M et al. Immature dendritic cells phagocytose apoptotic cells via alphavbeta5 and CD36, and cross-present antigens to cytotoxic T lymphocytes. J. Exp. Med. 1998; 188:1359-1368.
43. Albert M L, Sauter B, Bhardwaj N. Dendritic cells acquire antigen from apoptotic cells and induce class I-restricted CTL. Nature. 1998; 392: 86-89.
44. Fong L. and Engleman E G. Dendritic cells in cancer immunotherapy. Annu. Rev. Immunol. 2000; 18:245-273.
45. Fong L, Ruegg C L, Brockstedt D, Engleman E G, Laus R. Induction of tissue specific autoimmune prostatis with prostatic acid phosphatase immunization: implications for immunotherapy of prostate cancer. J. Immunol. 1997; 159: 3113-17.
46. Toungouz M, Quinet C, Thille E, Fourez S, Pradier O, Delville J P, Velu T. Lambermont M. Cytotherapy 1999; 1: 447-453.

TABLE 1

Cytokine production by monocyte-derived DC

| Stimulation | Cells | Cytokine levels (ng/ml) | | | | |
|---|---|---|---|---|---|---|
| | | TNFα | IL-6 | IL-8 | IL-12 (p40) | IL-12 (p70) |
| None | GM-CSF/IL-4 | 0.59 ± 0.26 | 0.31 ± 0.16 | 1.73 ± 0.75 | <0.02 | <0.01 |
| | IL-3/IFN-β | 0.81 ± 0.21 | 0.86 ± 0.17 | 6.40 ± 2.95* | 0.29 ± 0.13 | <0.01 |
| LPS | GM-CSF/IL-4 | 32.9 ± 7.13 | 16.6 ± 4.97 | 88.0 ± 14.3 | 68.7 ± 20.0 | 0.04 ± 0.01 |
| | IL-3/IFN-β | 18.1 ± 3.22* | 11.6 ± 2.59 | 69.6 ± 13.3 | 3.8 ± 1.53* | <0.01* |
| 3T6 | GM-CSF/IL-4 | 0.56 ± 0.55 | 0.45 ± 0.25 | 3.45 ± 1.27 | 0.12 ± 0.05 | <0.01 |
| | IL-3/IFN-β | 1.08 ± 1.08 | 0.12 ± 0.10 | 12.0 ± 2.88* | 0.03 ± 0.02 | <0.01 |
| 3T6-40L | GM-CSF/IL-4 | 2.86 ± 0.80 | 2.55 ± 0.45 | 15.0 ± 2.79 | 43.0 ± 19.0 | 0.38 ± 0.14 |
| | IL-3/IFN-β | 4.06 ± 0.81 | 7.46 ± 2.17* | 117.2 ± 41.1* | 7.41 ± 1.50* | 0.03 ± 0.01* |

*p <0.05 as compared to DC generated in GM-CSF and IL-4 (Wilcoxon's test).

TABLE 2

Poly (I:C) induces IFN-α production by IL-3/IFN-β DC

| Stimulation | n | IFN-α level (pg/ml) |
|---|---|---|
| None | 11 | <12 |
| 3T6-CD40L | 11 | <12 |
| LPS | 11 | 41 ± 9 |
| Influenza virus | 6 | 90 ± 48 |
| Poly (I:C) | 11 | 1873 ± 236 |

The invention claimed is:

1. A method for differentiation and maturation of isolated monocytes into stimulated IL3-R+CD11c+ myeloid dendritic cells consisting of (a) incubating said monocytes with a combination of IFN-β and IL-3 and (b) incubating the IL3-R+ CD11c+ myeloid dendritic cells with a stimulant chosen from a group consisting of virus, bacterium, lipopolysaccharide (LPS), nucleic acid, and a combination thereof.

2. A method for differentiation and maturation of isolated monocytes into stimulated IL3-R+CD11c+ myeloid dendritic cells consisting of (a) incubating said monocytes with a combination of IFN-β and IL-3 and (b) incubating the IL3-R+ CD11c+ myeloid dendritic cells with poly (I:C).

3. The method according to claim 1, wherein IL-3 is present at a concentration between 1 and 1000 U/ml.

4. The method according to claim 3, wherein IL-3 is present at a concentration of 50 U/ml.

5. The method according to claim 2, wherein IL-3 is present at a concentration between 1 and 1000 U/ml.

6. The method according to claim 5, wherein IL-3 is present at a concentration of 50 U/ml.

7. The method according to claim 1, wherein the stimulant is a virus.

8. The method according to claim 1, wherein the stimulant is a bacterium.

9. The method according to claim 1, wherein the stimulant is LPS.

10. The method according to claim 1, wherein the stimulant is a nucleic acid.

* * * * *